United States Patent
Xia et al.

(10) Patent No.: US 11,963,832 B2
(45) Date of Patent: Apr. 23, 2024

(54) SYSTEMS AND METHODS FOR COMPUTER-AIDED ORTHOGNATHIC SURGICAL PLANNING

(71) Applicant: THE METHODIST HOSPITAL, Houston, TX (US)

(72) Inventors: James Jiong Xia, Houston, TX (US); Jaime Gateno, Bellaire, TX (US); Peng Yuan, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

(21) Appl. No.: 18/079,277

(22) Filed: Dec. 12, 2022

(65) Prior Publication Data

US 2023/0111070 A1 Apr. 13, 2023

Related U.S. Application Data

(63) Continuation of application No. 16/326,458, filed as application No. PCT/US2017/047805 on Aug. 21, 2017, now Pat. No. 11,523,886.

(Continued)

(51) Int. Cl.
*G06T 7/00* (2017.01)
*A61B 34/10* (2016.01)
(Continued)

(52) U.S. Cl.
CPC .......... *A61C 13/0004* (2013.01); *A61B 34/10* (2016.02); *A61B 34/20* (2016.02);
(Continued)

(58) Field of Classification Search
CPC .................................................. G06T 7/0014
See application file for complete search history.

(56) References Cited

U.S. PATENT DOCUMENTS 6,213,769 B1   4/2001   Bettega et al.
6,671,539 B2  12/2003   Gateno et al.
(Continued)

FOREIGN PATENT DOCUMENTS

CN      1998022 A    7/2007
CN    101706844 A    5/2010
(Continued)

OTHER PUBLICATIONS

Office action from corresponding Brazilian Patent Application No. BR112019003279-7, dated Mar. 21, 2023 (with English-language translation).

(Continued)

*Primary Examiner* — Edward Park
(74) *Attorney, Agent, or Firm* — Meunier Carlin & Curfman LLC

(57) ABSTRACT

Systems and methods for orthognathic surgical planning are described herein. An example computer-implemented method can include generating a composite three-dimensional (3D) model of a subject's skull, defining a primal reference frame for the composite 3D model, performing a cephalometric analysis on the composite 3D model to quantify at least one geometric property of the subject's skull, performing a virtual osteotomy to separate the composite 3D model into a plurality of segments, performing a surgical simulation using the osteotomized segments, and designing a surgical splint or template for the subject.

4 Claims, 18 Drawing Sheets

Related U.S. Application Data

(60) Provisional application No. 62/377,084, filed on Aug. 19, 2016.

(51) Int. Cl.
*A61B 34/20* (2016.01)
*A61C 13/00* (2006.01)

(52) U.S. Cl.
CPC ........ *A61C 13/0019* (2013.01); *G06T 7/0014* (2013.01); *A61B 2034/102* (2016.02); *A61B 2034/105* (2016.02); *A61B 2034/107* (2016.02); *A61B 2034/2068* (2016.02); *G06T 2207/30036* (2013.01); *G06T 2207/30204* (2013.01)

(56) References Cited

U.S. PATENT DOCUMENTS

| | | | |
|---|---|---|---|
| 7,792,341 | B2 | 9/2010 | Schutyser |
| 2003/0065259 | A1 | 4/2003 | Gateno et al. |
| 2003/0211441 | A1 | 11/2003 | Mauro |
| 2005/0022158 | A1 | 1/2005 | Launay |
| 2006/0079759 | A1 | 4/2006 | Vaillant et al. |
| 2007/0092126 | A1 | 4/2007 | Fang et al. |
| 2007/0197902 | A1 | 8/2007 | Schutyser |
| 2008/0021502 | A1 | 1/2008 | Imielinska et al. |
| 2009/0028403 | A1 | 1/2009 | Bar-Aviv et al. |
| 2009/0311647 | A1 | 12/2009 | Fang et al. |
| 2012/0257841 | A1 | 10/2012 | Liao |
| 2013/0187905 | A1 | 7/2013 | Vaddadi et al. |
| 2014/0348405 | A1 | 11/2014 | Chen et al. |
| 2016/0238385 | A1* | 8/2016 | Ohtomo ................ G01S 7/4817 |
| 2017/0000564 | A1 | 1/2017 | Gordon et al. |
| 2020/0320749 | A1 | 10/2020 | Vlachomitriou |
| 2022/0046369 | A1 | 2/2022 | Kristensen |
| 2022/0071671 | A1 | 3/2022 | Little et al. |

FOREIGN PATENT DOCUMENTS

| | | |
|---|---|---|
| CN | 103106348 A | 5/2013 |
| CN | 104203144 A | 12/2014 |
| CN | 104540466 A | 4/2015 |
| CN | 105078586 A | 11/2015 |
| CN | 105608741 A | 5/2016 |
| JP | 2008-503280 | 2/2008 |
| JP | 5020816 B9 | 9/2012 |
| WO | 03/028577 | 4/2003 |
| WO | 2008080235 A1 | 7/2008 |

OTHER PUBLICATIONS

Office action from corresponding Chinese Patent Application No. 201780064319.2, dated Nov. 16, 2022 (with English-language translation).
Office action from corresponding Chinese Patent Application No. 201780064319.2, dated Jun. 8, 2023 (with English-language translation).
Office action from corresponding European Patent Application No. 17842265.5, dated Apr. 6, 2023.
Office action from corresponding Israeli Patent Application No. 264881, dated Apr. 4, 2022.
Office action from corresponding Japanese Patent Application No. 2019-530376, dated Apr. 4, 2023 (with English-language translation).
Yuan P, et al., A Novel Computer-Aided Surgical Simulation (CASS) System to Streamline Orthognathic Surgical Planning, 18th International Conference, Austin, TX; Lecture Notes in Computer Science, Aug. 14, 2016.
Office action from corresponding Canadian Patent Application No. 3072415, dated Aug. 3, 2023.
International Search Report and Written Opinion in PCT/US2017/047805, dated Nov. 30, 2017, 11 pages.
Examination report issued for Australian Application No. 2017312214, dated Nov. 29, 2021.
Examination Report issued for Indian Application No. 201927010310, dated Jun. 4, 2021. English Translation Included.
Office Action issued for Japanese Application No. 2019-530376, dated Sep. 7, 2021. English Translation Included.
Extended European Search Report issued for U.S. Appl. No. 17/842,265, dated Jan. 29, 2020.
Office Action issued for Korean Application No. 10-2019-7007567, dated Apr. 6, 2022. English Translation Included.
Office Action, dated Jul. 26, 2022, received in connection with corresponding JP Patent Application No. 2019-530376 (with English-language translation).
Fujinami, J., et al., "Research on the Facial Symmetry of Japanese People—Standard Diagram of Posterior-anterior Roentgenographic Cephalometrics," The Japanese Journal of Jaw Deformities, vol. 15, No. 2, (Aug. 2005), pp. 68-77 (with English-language abstract).
Notice of Allowance dated Oct. 28, 2022 for corresponding Korean Patent App. No. 10-2019-7007567, 4 pages (with English-language translation).
Office Action dated Oct. 19, 2022 for corresponding Canadian Patent App. No. 3,072,415, 4 pages.
Office Action dated Feb. 3, 2023 for corresponding Mexican Patent App. No. MX/a/2019/002037, 5 pages (with English-language translation).
Bobek, S., et al., Virtual surgical planning for orthognathic surgery using digital data transfer and an intraoral fiducial marker: the charlotte method. J Oral Maxillofac Surg, 2015. 73(6): p. 1143-58.
Chang YB, Xia JJ, Gateno J, Xiong Z, Teichgraeber JF, Lasky RE, Zhou X (2012) In vitro evaluation of new approach to digital dental model articulation. J Oral Maxillofac Surg, 70 (4):952-962. doi: 10.1016/j.joms.2011.02.109.
Chang YB, Xia JJ, Gateno J, Xiong Z, Zhou X, Wong ST (2010) An automatic and robust algorithm of reestablishment of digital dental occlusion. IEEE Trans Med Imaging 29 (9):1652-1663. doi:10.1109/TMI.2010.2049526.
Damstra J, Fourie Z, Ren Y (2010) Simple technique to achieve a natural position of the head for cone beam computed tomography. Br J Oral Maxillofac Surg 48 (3):236-238. doi:10.1016/j.bjoms. 2009.10.001.
Gateno J, Xia J, Teichgraeber JF, Rosen A, Hultgren B, Vadnais T (2003) The precision of computer-generated surgical splints. J Oral Maxillofac Surg 61 (7):814-817.
Gateno J, Xia JJ, Teichgraeber JF (2011) Effect of facial asymmetry on 2-dimensional and 3-dimensional cephalometric measurements. J Oral Maxillofac Surg 69 (3):655-662. doi:10.1016/j.joms.2010. 10.046.
Gateno J, Xia JJ, Teichgraeber JF (2011) New Methods to Evaluate Craniofacial Deformity and to Plan Surgical Correction. Semin Orthod 17 (3):225-234. doi:10.1053/j.sodo.2011.02.006.
Gateno J, Xia JJ, Teichgraeber JF, Christensen AM, Lemoine JJ, Liebschner MA, Gliddon MJ, Briggs ME (2007) Clinical feasibility of computer-aided surgical simulation (CASS) in the treatment of complex cranio-maxillofacial deformities. J Oral Maxillofac Surg 65 (4):728-734.
Gateno, J., et al., A new technique for the creation of a computerized composite skull model. J Oral Maxillofac Surg, 2003. 61(2): p. 222-7.
Gateno, J., et al., The primal sagittal plane of the head: a new concept. Int J Oral Maxillofac Surg, 2016. 45(3): p. 399-405.
Gateno, J., J.J. Xia, and J.F. Teichgraeber, New 3-dimensional cephalometric analysis for orthognathic surgery. J Oral Maxillofac Surg, 2011. 69(3): p. 606-22.
Gottschalk S, Lin MC, Manocha D (1996) OBBTree: a hierarchical structure for rapid interference detection. Paper presented at the Proc. of ACM Siggraph '96.
Hsu, S.S., et al., Accuracy of a computer-aided surgical simulation protocol for orthognathic surgery: a prospective multicenter study. J Oral Maxillofac Surg, 2013. 71(1): p. 128-42.
Li et al., New approach to establish an object reference frame for dental arch in computer-aided surgical simulation, Int. J. Oral Maxillofac. Surg. 2017.

(56) References Cited

OTHER PUBLICATIONS

Lorensen WE, Cline HE Marching cubes: A high resolution 3D surface construction algorithm. In: SIGGRAPH '87 Proceedings of the 14th Annual Conference on Computer Graphics and Interactive Techniques, New York, NY, 1987. ACM SIGGRAPH Computer Graphics.

Schatz EC (2006) A new technique for recording natural head position in three dimensions (MS thesis). The University of Texas Health Science Center at Houston, Houston (Advisors: Xia JJ, English JD, Garrett FA, et al.), 149 pages.

Schatz EC, Xia JJ, Gateno J, English JD, Teichgraeber JF, Garrett FA (2010) Development of a technique for recording and transferring natural head position in 3 dimensions. J Craniofac Surg 21 (5):1452-1455. doi: 10.1097/SCS.0b013e3181ebcd0a.

Swennen GR, Barth EL, Eulzer C, Schutyser F (2007) The use of a new 3D splint and double CT scan procedure to obtain an accurate anatomic virtual augmented model of the skull. Int J Oral Maxillofac Surg 36 (2):146-152.

Swennen GR, Schutyser F (2006) Three-dimensional cephalometry: spiral multi-slice vs cone-beam computed tomography. Am J Orthod Dentofacial Orthop 130 (3):410-416.

Swennen GR, Schutyser F, Barth EL, De Groeve P, De Mey A (2006) A new method of 3-D cephalometry Part I: the anatomic Cartesian 3-D reference system. J Craniofac Surg 17 (2):314-325.

Xia J, Ip HH, Samman N, Wang D, Kot CS, Yeung RW, Tideman H (2000) Computer-assisted three-dimensional surgical planning and simulation: 3D virtual osteotomy. Int J Oral Maxillofac Surg 29 (1):11-17.

Xia J, Ip HH, Samman N, Wong HT, Gateno J, Wang D, Yeung RW, Kot CS, Tideman H (2001) Three-dimensional virtual-reality surgical planning and soft-tissue prediction for orthognathic surgery. IEEE Trans Inf Technol Biomed 5 (2):97-107.

Xia J, Samman N, Yeung RW, Shen SG, Wang D, Ip HH, Tideman H (2000) Three-dimensional virtual reality surgical planning and simulation workbench for orthognathic surgery. Int J Adult Orthodon Orthognath Surg 15 (4):265-282.

Xia JJ, Gateno J, Teichgraeber JF (2005) Three-dimensional computer-aided surgical simulation for maxillofacial surgery. Atlas Oral Maxillofac Surg Clin North Am 13 (1):25-39.

Xia, J.J., et al., A new method to orient 3-dimensional computed tomography models to the natural head position: a clinical feasibility study. J Oral Maxillofac Surg, 2011. 69(3): p. 584-91.

Xia, J.J., et al., Algorithm for planning a double-jaw orthognathic surgery using a computer-aided surgical simulation (CASS) protocol. Part 1: planning sequence. Int J Oral Maxillofac Surg, 2015. 44(12): p. 1431-40.

Xia, J.J., et al., Algorithm for planning a double-jaw orthognathic surgery using a computer-aided surgical simulation (CASS) protocol. Part 2: three-dimensional cephalometry. Int J Oral Maxillofac Surg, 2015. 44(12): p. 1441-50.

Xia, J.J., J. Gateno, and J.F. Teichgraeber, New clinical protocol to evaluate craniomaxillofacial deformity and plan surgical correction. J Oral Maxillofac Surg, 2009. 67(10): p. 2093-106.

Yuan, et al., Design, development and clinical validation of computer-aided surgical simulation system for streamlined orthognathic surgical planning, Int J CARS, 2017.

Zelditch ML, Swiderski DL, Sheets HD (2012) Geometric morphometrics for biologists: a primer. Elsevier, London, UK.

Yuan P, Ho DC-Y, Chang C-M, Li J, Mai H, Kim D, Shen S, Zhang X, Zhou X, Xiong Z, Gateno J, Xia JJ (2016) A Novel Computer-Aided Surgical Simulation (CASS) System to Streamline Orthognathic Surgical Planning, Medical Imaging and Augmented Reality: 7th International Conference, MIAR 2016, Bern, Switzerland, Aug. 24-26, 2016 (1 page).

Schatz, et al., "A New Technique for Recording Natural Head Position in Three Dimensions", 2006, pp. 36-52.

\* cited by examiner

SYSTEMS AND METHODS FOR COMPUTER-AIDED ORTHOGNATHIC SURGICAL PLANNING

CROSS-REFERENCE TO RELATED APPLICATIONS

This application is a continuation of U.S. patent application Ser. No. 16/326,458, filed on Feb. 19, 2019, which is a national stage application filed under 35 U.S.C. § 371 of PCT/US2017/047805, filed on Aug. 21, 2017, which claims the benefit of U.S. provisional patent application No. 62/377,084, filed on Aug. 19, 2016, and entitled "CEPHALOMETRY MODELING SYSTEM FOR SURGICAL PLANNING," the disclosures of which are expressly incorporated herein by reference in their entireties.

STATEMENT REGARDING FEDERALLY FUNDED RESEARCH

This invention was made with government support under Grant nos. RO1 DE022676 and RO1 DE021863 awarded by the National Institutes of Health/National Institute of Dental and Craniofacial Research. The government has certain rights in the invention.

BACKGROUND

Orthognathic surgery is a surgical procedure to correct dentofacial, or jaw, deformities. Each year thousands of patients elect to undergo various orthognathic surgical procedures. However, due to the complex nature of the dentofacial anatomy, orthognathic surgery often requires extensive presurgical planning. Whereas surgical techniques have seen rapid improvement in the last 50 years, e.g. rigid fixation, resorbable materials, and distraction osteogenesis, available orthognathic surgical planning tools have remained unchanged since the 1960s, e.g. two-dimensional (2D) cephalometry, prediction tracing and stone dental model surgery [1-3]. There are many documented problems associated with these traditional techniques, which have often led to less than optimal surgical outcomes [3].

To address the problems associated with traditional planning methods as described above, a clinical protocol using a computer-aided surgical simulation (CASS) method for planning orthognathic surgery has been developed [3,4]. This CASS protocol has proven to be imperative in producing a more accurate and effective treatment plan [5,6]. It is now a new standard of care. However, CASS protocol requires that the user have extensive experience using computer graphics and virtual simulations. These simulations would have to be outsourced to expensive commercial services, or individual doctors would have to be trained extensively to use off-the-shelf computer graphics software. In addition, there is no known planning system available with the capabilities of performing every task required for implementing CASS protocol, e.g. neutral head posture (NHP) registration, three-dimensional (3D) cephalometric analysis, automated surgical simulation, and designing splint/template for 3D printers.

SUMMARY

An example computer-implemented method for orthognathic surgical planning is described herein. The computer-implemented method can include generating a composite three-dimensional (3D) model of a subject's skull, defining a primal reference frame for the composite 3D model, performing a cephalometric analysis on the composite 3D model to quantify at least one geometric property of the subject's skull, performing a virtual osteotomy to separate the composite 3D model into a plurality of segments, performing a surgical simulation using the osteotomized segments, and designing a surgical splint or template for the subject. The composite 3D model can include a rendition of skeletal, dental, and soft tissue features of the subject's skull.

Alternatively or additionally, the composite 3D model can include a plurality of 3D models. Additionally, the plurality of 3D models can include two or more of a midface model, a mandible model, a soft tissue model, a dental model, or a fiducial marker model. In some implementations, the step of generating the composite 3D model can include merging the dental model with the midface and mandible models. In some implementations, the computer-implemented method can further include registering the plurality of 3D models that form the composite 3D model.

Alternatively or additionally, the step of defining the primal reference frame can include reorienting the composite 3D model to a standard anatomical posture of the subject.

Alternatively or additionally, the step of defining the primal reference frame can include calculating one or more planes of symmetry for the composite 3D model. The one or more planes of symmetry can be a midsagittal plane, an axial plane, or a coronal plane.

Alternatively or additionally, the step of performing the cephalometric analysis can include quantifying object symmetry of the subject's skull. The cephalometric analysis is performed on the composite 3D model, i.e., a 3D cephalometric analysis is performed. For example, a weighted Procrustes analysis can be used to quantify object symmetry of the subject's skull.

Alternatively or additionally, the step of performing the cephalometric analysis can include quantifying symmetrical alignment between a feature of the subject's skull and the primal reference frame. In some implementations, the step of quantifying symmetrical alignment between the feature of the subject's skull and the primal reference frame can further include determining an object reference frame for the feature of the subject's skull. Optionally, the feature of the subject's skull is a dental arch. In some implementations, the step of determining the object reference frame can further include using principal component analysis (PCA) based adaptive minimum Euclidean distances.

Alternatively or additionally, the computer-implemented method can further include generating a cephalometric analysis report including the at least one geometric property of the subject's skull before and after the surgical simulation.

Alternatively or additionally, the at least one geometric property can be symmetry, shape, size, position, and/or orientation.

Alternatively or additionally, the virtual osteotomy can further include defining a group of multi-connected hexahedrons in proximity to a location of the virtual osteotomy and separating the composite 3D model into the plurality of segments. The plurality of segments can include midface segment, Le Fort I segment and upper teeth, distal segment and lower teeth, chin segment, and/or left and right proximal segments.

Alternatively or additionally, the surgical simulation comprises a maxillary surgery, a mandibular surgery, or a mandibular chin surgery.

Alternatively or additionally, the step of performing the surgical simulation can further include defining a hierarchal structure for the osteotomized segments, establishing a final dental occlusion, and repositioning the osteotomized segments into a desired maxillomandibular combination. The final dental occlusion can achieve a maximum intercuspation between the subject's upper and lower teeth. In some implementations, the step of repositioning the osteotomized segments can further include translating and/or rotating the maxillomandibular combination in six degrees of freedom.

Alternatively or additionally, the surgical splint or template can be an intermediate splint for maxillary surgery with the subject's upper teeth in a desired position or for mandibular surgery with the subject's lower teeth in a desired position. Alternatively or additionally, the surgical splint or template can be a final splint with the subject's upper and lower teeth in a desired position.

Alternatively or additionally, the step of designing the surgical splint or template can further include generating a 3D model of the surgical splint or template, and printing the surgical splint or template using a 3D printer.

Alternatively or additionally, the computer-implemented method can further include displaying the composite 3D model on a display device.

Alternatively or additionally, the surgical simulation can further include performing an overcorrection by translating and/or rotating one or more of the osteotomized segments.

Alternatively or additionally, the computer-implemented method can further include assigning a respective unique identifier to each of a plurality of 3D objects. For example, a unique identifier can be assigned to each of a plurality of 3D models. Alternatively or additionally, a unique identifier can be assigned to each of a plurality of osteotomized segments. By assigning unique identifiers to 3D objects, a hierarchal structure can be created, which facilitates surgical simulation.

An example computer-implemented method for performing a symmetric analysis of a three-dimensional (3D) model is described herein. The computer-implemented method can include identifying a plurality of landmarks on the 3D model, where the landmarks define a cloud of points. The computer-implemented method can further include creating a mirror-image copy of the cloud of points, iteratively translating and/or rotating the mirror-image copy until fitted with the cloud of points, superimposing the mirror-image copy and the cloud of points to create a single group of points, and quantifying object symmetry of the 3D model based on the single group of points.

An example computer-implemented method for determining an object reference frame for a subject's dental arch is also described herein. The computer-implemented method can include digitizing a plurality of dental landmarks on a composite three-dimensional (3D) model of a subject's dental arch, creating respective right and left curves using the dental landmarks, resampling along the respective right and left curves to obtain a plurality of sample points, calculating an initial Cartesian coordinate system by applying a principle component analysis (PCA) to the sample points, translating the initial Cartesian coordinate system to a new origin and assigning a first axis (z-axis) of the object reference frame for the subject's dental arch, iteratively calculating a second axis (y-axis) of the object reference frame for the subject's dental arch, and calculating a third axis (x-axis) of the object reference frame for the subject's dental arch. The iterative calculation can minimize Euclidean distances. Additionally, the composite 3D model can include a rendition of skeletal, dental, and soft tissue features of the subject's dental arch.

Alternatively or additionally, the computer-implemented method can further include determining sagittal, axial, and coronal planes for the subject's dental arch.

Alternatively or additionally, the respective right and left curves include respective right and left sample point arrays, and the iterative calculation can minimize Euclidean distances between one of the respective right and left sample point arrays and a mirror-image copy of the other of the respective right and left sample point arrays.

Alternatively or additionally, a number of sample points can be greater than a number of dental landmarks.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 7A (before view) illustrates how the hierarchy is used to organize bony segments and make sure all related segments are moved/rotated together. FIG. 7B (after view) illustrates the 3D cephalometry window with measurements being updated in real time during surgical simulation.

FIG. 8A illustrates the contour of the top face of an example surgical splint being traced onto a plane. FIG. 8B illustrates using the top and bottom contours, as well as, extensions if necessary, to generate the surgical splint by the AnatomicAligner.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for orthognathic surgical planning, it will become evident to those skilled in the art that the implementations are not limited thereto.

As described above, there are many problems associated with traditional surgical planning methods for orthognathic surgery. To address these problems, a computer-aided surgical simulation (CASS) system has been developed to plan orthognathic surgery following a streamlined clinical protocol. An example orthognathic surgical planning system can include a plurality of modules: (1) a three-dimensional (3D) model module, (2) a reference frame module, (3) a 3D cephalometric analysis module, (4) a virtual osteotomy module, (5) a surgical simulation module, and (6) a surgical splint module. This disclosure contemplates that the example orthognathic surgical planning system can be implemented using a computing device such as computing device 1100 shown in FIG. 11.

Figure 11:
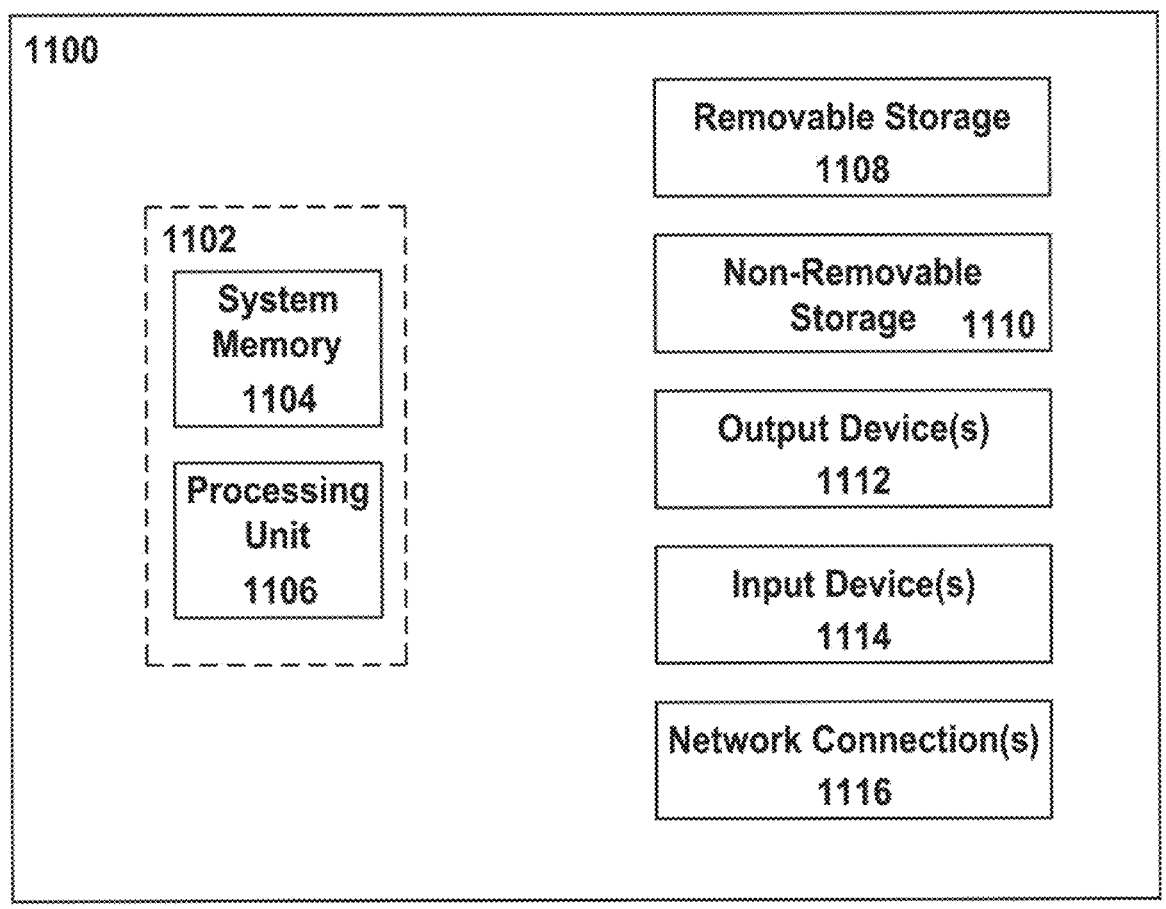
FIG. 11 is a block diagram of an example computing device.

The 3D model module can be configured to generate a composite 3D model of a subject's skull, where the composite 3D model includes a rendition of skeletal, dental, and soft tissue features of the subject's skull. Optionally, the composite 3D module can be displayed on a display device (e.g., output device 1112 as shown in FIG. 11). This disclosure contemplates that the composite 3D module can be displayed during one or more aspects of surgical planning, e.g., during 3D cephalometric analysis, virtual osteotomy, surgical simulation, and/or splint design. As described below, the 3D model module can be configured for image (e.g., computed tomography (CT) or other medical image) segmentation and 3D model reconstruction. This disclosure contemplates using image segmentation and 3D model reconstruction algorithms, which are known in the art. The reference frame module can be configured to generate a primal reference frame of the composite 3D model, e.g., by registration and reorientation of models to a standard anatomical posture such as neutral head posture (NHP) as described below. Alternatively or additionally, the primal reference frame module can be configured to calculate one or more planes of symmetry (e.g., a midsagittal plane, an axial plane, and/or a coronal plane) for the composite 3D model as described below.

The 3D cephalometric analysis module can be configured to quantify at least one geometric property of the subject's skull. These analyses can be performed on the composite 3D module. The geometric property can include, but is not limited to, symmetry, shape, size, position, and/or orientation of the subject's skull. This includes object symmetry and symmetrical alignment measurements as described in implementations below. Optionally, the results of the cephalometric analysis can be provided to a user (e.g., a surgeon) and/or displayed on a display device (e.g., output device 1112 as shown in FIG. 11). The virtual osteotomy module can be configured to separate the composite 3D model into a plurality of segments. The segments can include, but are not limited to, midface segment, Le Fort I segment and upper teeth, distal segment and lower teeth, chin segment, and/or left and right proximal segments. The virtual osteotomy can be performed on the composite 3D model by defining a group of multi-connected hexahedrons in proximity to a location of the virtual osteotomy as described below. The surgical simulation module can be configured to perform the surgery on the osteotomized segments, e.g., by repositioning, translating, and/or or rotating the osteotomized segments to achieve a desired maxillomandibular combination as described below. The surgical simulation can be any orthognathic surgery such as a maxillary surgery, a mandibular surgery, or a mandibular chin surgery, for example. The surgical splint module can be configured to design a surgical splint or template for the subject. Surgical splints or templates are used to transfer the computerized surgical plan to the subject at the time of the actual surgery. A surgical splint is a horseshoe-shaped teeth-anchored wafer that is placed between the subject's upper and lower teeth. Optionally, the surgical splint module can generate a 3D model of the surgical splint or template, which can then be printed using a 3D printer, as described below. This disclosure contemplates using any 3D printer known in the art including, but not limited to, OBJECT30 ORTHODESK from Stratasys Ltd. of Eden Prairie, MN. In addition, the splint or template can be printed using FDA approved biocompatible materials such as MED610 material. It should be understood that the example 3D printer and/or biocompatible material are provided only as examples and that others can be used with the example orthognathic surgical planning system described herein.

One example orthognathic surgical planning system described herein is referred to as the AnatomicAligner. The AnatomicAligner is a multiprocessing computation-based system. The AnatomicAligner software was programmed using object-oriented programming (OOP) utilizing MICROSOFT VISUAL C++ from MICROSOFT CORP. of Redmond, WA, the Visualization Toolkit (VTK), which is open source 3D computer graphics software created by Kitware, Inc. of Clifton Park, NY, and Insight Segmentation and Registration Toolkit (ITK), which is open source medical image analysis software created by the Insight Software Consortium (ISC). The user interface for the AnatomicAligner is wizard-driven. It should be understood that the orthognathic surgical planning system and/or the AnatomicAligner can be implemented using hardware and/or software other than those described in the examples below.

The AnatomicAligner described herein includes six modules: image segmentation and three-dimensional (3D) reconstruction, registration and reorientation of models to neutral head posture (NHP), 3D cephalometric analysis, virtual osteotomy, surgical simulation, and surgical splint generation. The accuracy of the AnatomicAligner was validated in a stepwise fashion: first to evaluate the accuracy of AnatomicAligner using 30 sets of patient data, then to evaluate the fitting of splints generated by AnatomicAligner using 10 sets of patient data. The industrial gold standard system, MATERIALISE MIMICS from Materialise NV of Leuven, Belgium, was used as the reference.

When comparing the results of segmentation, virtual osteotomy and transformation achieved with AnatomicAligner to the ones achieved with the MATERIALISE MIMICS system, the absolute deviation between the two systems was clinically insignificant. The average surface deviation between the two models after 3D model reconstruction in AnatomicAligner and the MATERIALISE MIMICS system was 0.3 mm with a standard deviation (SD) of 0.03 mm. All the average surface deviations between the two models after virtual osteotomy and transformations were smaller than 0.01 mm with a SD of 0.01 mm. In addition, the fitting of splints generated by AnatomicAligner were at least as good as the ones generated by the MATERIALISE MIMICS system.

Figure 1:
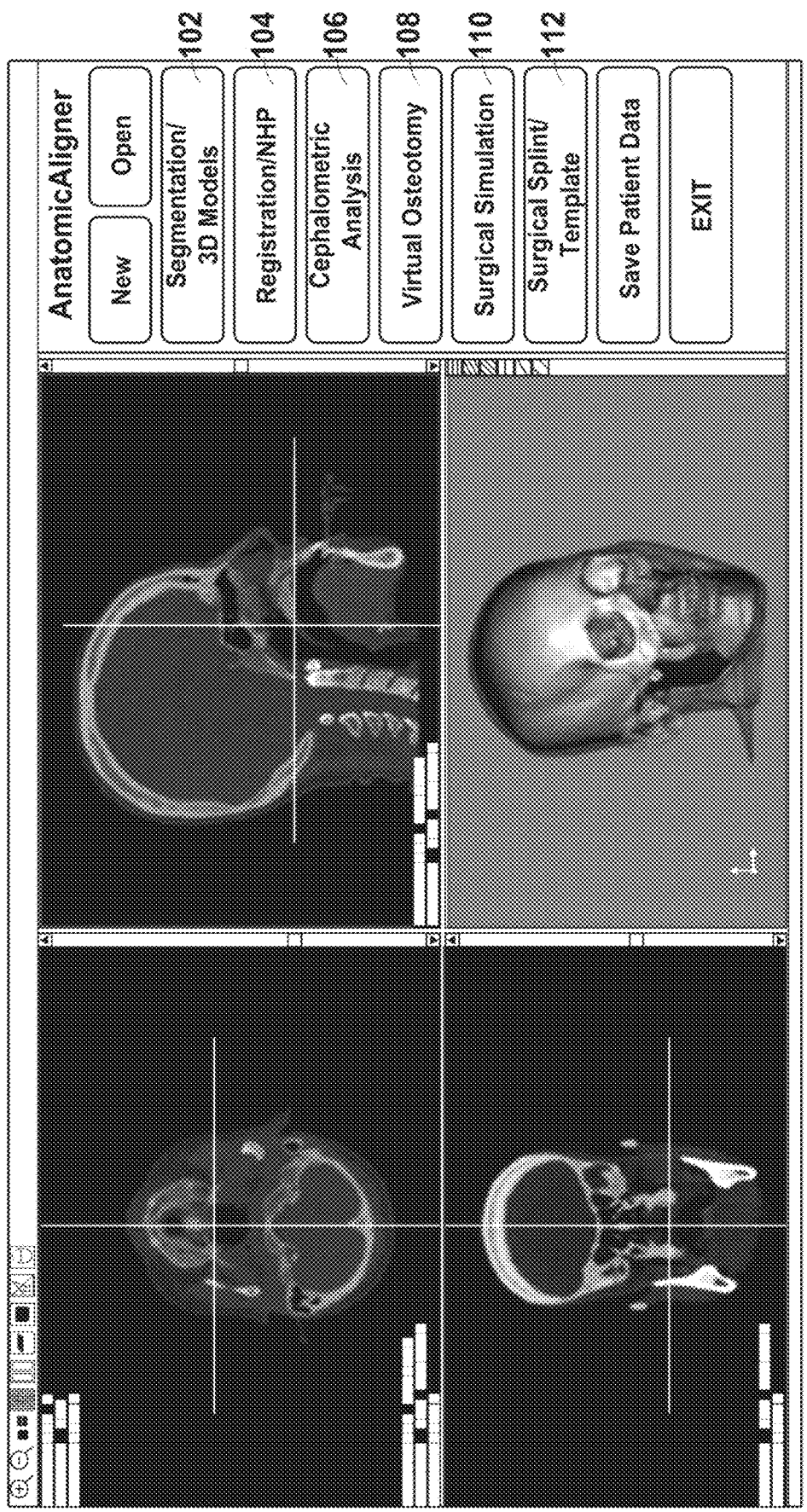
FIG. 1 illustrates an example main user interface of the AnatomicAligner system according to implementations described herein.

Referring now to FIG. 1, the AnatomicAligner includes the following modules. In the Segmentation/3D Models module 102, CT dataset are imported for segmentation and 3D model reconstruction. In the Registration/NHP module 104, a composite skull model is constructed to accurately render skeleton, dentition, and facial soft tissues [8]. In addition, the primal reference frame for surgical planning is established, i.e., placing all the models in a unique 3D coordinate system [9-13]. In the 3D Cephalometric Analysis module 106, 3D cephalometry [9,14], which solves many problems associated with current 2D and purported 3D cephalometry, is performed. In the Virtual Osteotomy module 108, various osteotomies (cuts) to the 3D bones are performed to simulate orthognathic surgery [3,4,15-18]. In the Surgical Simulation module 110, a surgical plan is formulated. The optimal surgery is chosen based on both visual results and mathematical calculations. Finally in the Surgical Splint/Template module 112, surgical guides, including splints and templates, are designed to guide surgeons during surgery [19,20]. The computerized surgical plan is transferred to the patient intraoperatively through 3D printed surgical guides, the splints and templates. The details of each module are described in detail below.

Module 1: 2D Segmentation and 3D Model Reconstruction

The purpose of the Segmentation/3D Models module 102 is to generate a group of 3D models capable of displaying an accurate rendering of the skeleton and facial soft tissue for surgical planning. First, CT scans following the Digital Imaging and Communications in Medicine (DICOM) standard are imported into the system. It should be understood that CT images are provided as examples. This disclosure contemplates using other medical images with the AnatomicAligner. Then, segmentation tools, including thresholding, regional thresholding, manual editing, region growing, and Boolean operations, are used to create masks for individual models (e.g. maxilla, mandible). Finally, the resulting masks are used to generate 3D surface models using Marching Cubes algorithm [21]. It should be understood that 3D surface models are used as opposed to volumetric renderings. 3D surface models are used for the 3D printing process. The printed surgical guides (e.g., splints or templates) play an important role in transferring the surgical plan to the patient at the time of surgery (refer to module 6).

In order to plan an orthognathic surgery, at least four CT models are generated: midface, mandible, soft tissue, and fiducial markers [4]. In addition, high resolution upper and lower digital dental models and their fiducial markers are imported. AnatomicAligner also includes a predefined hierarchy that incorporates each 3D model. Once a unique name is assigned to a 3D object, it is automatically placed within the hierarchical structure. This system defined hierarchy ensures ease of use during surgical simulation (refer to module 5).

Module 2: Model Registration and Reorientation to NHP

There are two main functions in the Registration/NHP module 104. The first is to construct the composite skull model, which accurately renders bones, soft tissues, and teeth for surgical planning. High resolution digital dental models are used for the composite skull, because 3D CT models do not produce highly accurate virtual replicas of the teeth [3,4,8]. In CT scans, teeth are often affected by artifacts from orthodontic braces, wires and bands, and dental restoration materials (e.g., amalgam). Therefore, the inaccurate CT teeth can be replaced with the highly accurate digital dental models. These models are generated using high-resolution laser scans or cone-beam CT scans [4]. Correctly assembling the digital dental models and CT models is done by registering the fiducial markers of the dental models to the corresponding fiducial markers of the CT bone models. Automatic (iterative closest point), semi-automatic (paired landmarks), and manual registration tools are implemented to register 3D models. In addition, the registration process uses the hierarchical structure to ensure that correlated models are collectively selected and then moved and rotated together [16,22].

The second function is to define a global reference frame (global Cartesian coordinate system) for the head [9,10,14]. The global reference frame is sometimes referred to herein as a "primal reference frame." The global reference frame is defined using the following steps: 1) establishing the correct orientation of the head, e.g., a standard anatomical posture, and 2) defining the correct position of the midsagittal, coronal, and axial planes of the reference frame. An example standard anatomical posture is neutral head posture (NHP).

NHP refers to the head orientation where the patient's head is relaxed and the visual axis is parallel to the floor. By establishing NHP, the digital environment directly reflects the clinical environment, as if the surgeon is actually examining the patient. NHP can be recorded using a digital orientation sensor [12,13], a self-leveling laser [5,23], or the standardized photograph method [3] during the patient's clinical examination. The clinically recorded NHP, in pitch, roll, yaw, is then applied to the original data space, mapping the entire original 2D and 3D datasets into the patient's NHP. Since the transformation matrix is saved in the system, the mapping of NHP can be adjusted or reset as necessary, at any time prior to surgical simulation. After establishing NHP, the next step, in establishing the global reference frame, is to define the midsagittal plane. This is an important clinical step. Ideally, the midsagittal plane should divide the head evenly into the right and left halves, acting as the plane of symmetry between them. The midsagittal plane is determined based on either a mix of clinical measurements and the doctor's judgement [3,4,9,14] or a mathematical algorithm [10]. Subsequently, the head is further divided into upper and lower halves and front and back halves by the axial and coronal planes, respectively. These two planes are perpendicular to the midsagittal plane and pass through the midpoint of the right and left portions, the most superior anatomical landmark of the left and right external meatus. In the following steps, all calculations are carried out in the global reference frame, unless stated otherwise.

Module 3: 3D Cephalometry

In the 3D Cephalometric Analysis module 106, 3D cephalometric analysis [9,24] is incorporated into the AnatomicAligner. Cephalometry, or cephalometric analysis, is a group of anatomical landmark-based measurements used to quantify deformities of the head and facial units (e.g., midface, maxilla or mandible). Traditionally, cephalometric analysis is performed two-dimensionally on a cephalogram (a 2D plain radiograph that is acquired in a calibrated condition), where all the 3D anatomical structures are projected onto a 2D plane (either sagittal or coronal) [25]. There are many documented problems associated with 2D cephalometry [3,9,26-28].

The recent introduction of low-radiation low-cost cone-beam computed tomography (CBCT) scanners has promoted the usage of 3D images in an office setting. 3D cephalometry based on CBCT or CT scans can correct the problems associated with its 2D counterpart. However, 3D cephalometry is more complicated than just giving 2D analysis a "third" dimension [29]. Besides the global reference frame for the head, it also requires building local reference frames, explained below, for each individual facial unit and bony model. Optimal 3D cephalometry can include all five geometric properties: symmetry, shape, size, position and orientation. 3D cephalometry implemented in AnatomicAligner is achieved in the following steps.

Define the Cephalometric Analysis Scheme 3D cephalometric analysis is a modular system. An example 3D cephalometric analysis is shown in Table 1 below. All measurements are displayed in a grid, where they are grouped by geometric property (e.g., object symmetry, shape, size, position, and orientation), as well as anatomical location (e.g. mandible, maxilla, etc.) [9,16]. Other descriptive information of cephalometric analysis, e.g., name, description, facial unit category, measurements/landmarks used, is stored in a database file.

TABLE 1

3D Cephalometric Analysis

| Parameters | | Maxilla | Mandible Whole | Chin |
|---|---|---|---|---|
| | Object Symmetry | | | |
| | Shape | | | |
| Size | Length | | | |
| | Width | | | |
| | Height | | | |
| Position | Anteroposterior | | | |
| | Vertical | | | |
| | Transverse | Symmetrical | | |
| Orientation | Yaw | Alignment | | |
| | Roll | | | |
| | Pitch | | | |

Symmetry analysis encompasses measurements for both object symmetry and symmetrical alignment [9,14]. In human anatomy, object symmetry refers to the intrinsic local mirror symmetry of each facial unit. The object symmetry of a facial unit is analyzed by triangular technique and standard or weighted Procrustes analysis. Symmetrical alignment refers to the alignment of each facial unit with respect to the midsagittal plane of the head, in the global reference frame. This measurement requires an object reference frame for the facial unit to be measured. The object reference frame is established using triangular technique, principal component analysis based adaptive minimum Euclidean distances (PA-MED), or standard principal component analysis (PCA) [9,10,29]. The degree of symmetrical alignment of a facial unit is quantified by comparing the object reference frame to the global reference frame [9]. First, the transverse (right-left) deviation to the midsagittal plane is measured, and then the yaw and roll of the facial unit are measured using 3D orientation measurement as described below.

Shape is a geometric property unaffected by changes in size, position, and orientation. Shape is analyzed using Procrustes or weighted Procrustes analysis [9]. It is the method that most clearly shows distortions in shape, since two objects are scaled to the same size, placed in the same location, and rotated into alignment. For example, a patient's mandible is compared to the averaged mandible of a population with the same ethnicity, gender, and age.

Size measurement in 3D cephalometry is determined using linear measurements: length, width, and height. It is an intrinsic property of the object that is unrelated to the space the object occupies. It is simply the distance between two landmarks.

Position is the location occupied by the object in space. It is a relative measurement between the object-global or object-object reference frames. It is measured using either a Cartesian system (x, y, z) or a cylindrical coordinate system (radius, theta, transverse distance) [9,14].

Finally, orientation is also a relative measurement in either the object-global or object-object coordinate systems. The measurement is measured as the rotation from a reference position (global or object) to the current position (object). However a 3D composite angle is clinically meaningless [3]. Therefore, AnatomicAligner measures orientation using Tait-Bryan angles following a specific order—first yaw, then roll, and finally pitch, since these rotations are not commutative. This method minimizes the influence from yaw and roll during the pitch measurement. This is because only values of pitch have clinical significance, whereas the clinically ideal values of both yaw and roll should be zero.

Digitize Landmarks and Record their Initial Coordinates

All cephalometric measurements are based on manually digitized (placed) anatomical landmarks. The system includes a library with 178 of the most frequently used cephalometric landmarks. The landmark library can optionally be customized by adding additional landmarks as desired. In AnatomicAligner, only the landmarks used by the desired measurements need to be digitized. During the landmark digitization, a template window appears, displaying the anatomical location on a generic 3D model, to help users identify the correct position of the digitize landmarks.

Digitized landmarks are also linked to corresponding 3D models. When a 3D model is osteotomized (cut) into separate pieces (refer to module 4), linked landmarks are automatically inherited by the new models. This feature enables surgical simulation. The cephalometric measurements are automatically updated in real-time, while the bony segments are moved and rotated to the desired position.

Report Calculated Results

The results of the desired measurements are displayed in a floating window and automatically updated in real-time when bony segments and their linked landmarks are moved and/or rotated into a new location. A cephalometric analysis report, including measurements and the transformation matrix of each landmark before and after surgical simulation, can be generated. This disclosure contemplates that the cephalometric analysis report can be provided to a user, e.g., printed and/or displayed on a display device (e.g., output device 1112 as shown in FIG. 11).

Module 4: Virtual Osteotomy

Virtual osteotomy, which is performed by the Virtual Osteotomy module 108, is a fundamental function of the AnatomicAligner system. Its job is to cut a 3D bone model into two bony models (medically called "segments"). During the osteotomy, a user defines a line of landmarks indicating where the osteotomy should take place. These landmarks are used to create a multi-connected hexahedron cutting plane, the virtual "knife". The virtual osteotomy is then completed by classifying triangles that intersect with the multi-connected hexahedrons, creating new triangles to replace the "broken" triangle, and separating the osteotomized model into two new bony segments. Finally, the two new 3D bony segments are nested into the hierarchical structure under their parent model. At the end of the osteotomies, users have at least the following bony segments, for a typical orthognathic surgical simulation: midface, maxillary Le Fort I segment with upper teeth, mandibular distal segment with lower teeth, and the left and right proximal segments. The steps to achieve virtual osteotomy are described in detail below.

Form a Virtual Knife

Figure 2:
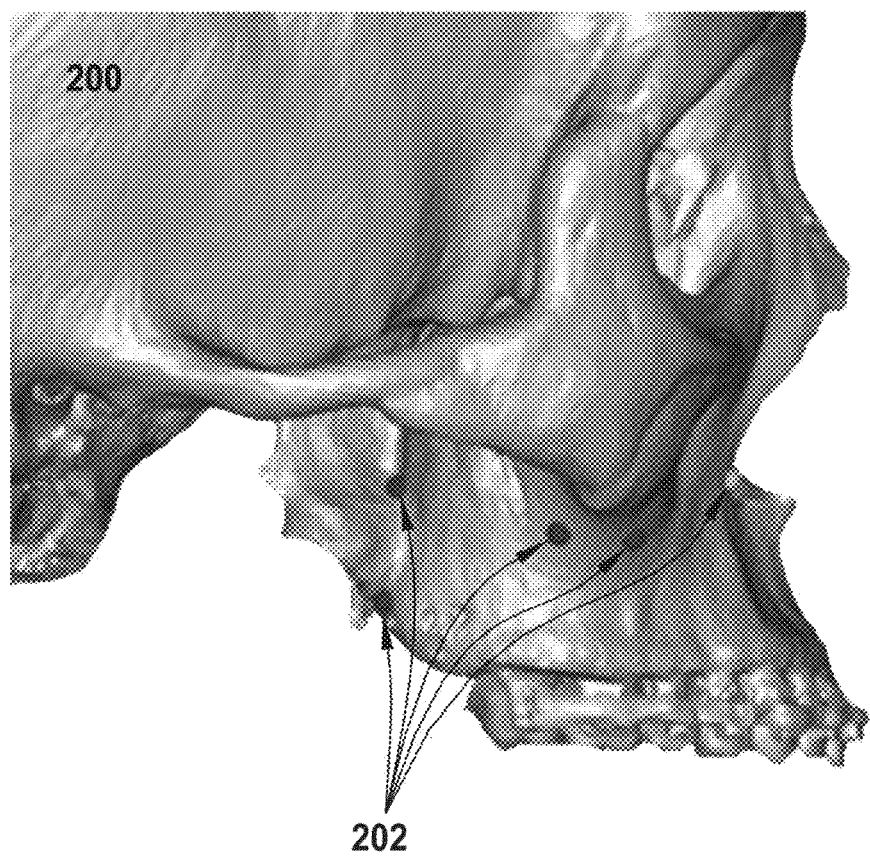
FIG. 2 illustrates digitized landmarks for generating a user defined cutting plane on an example composite 3D model of the subject's skull. The right-most dot is the last digitized point.
Figure 3:
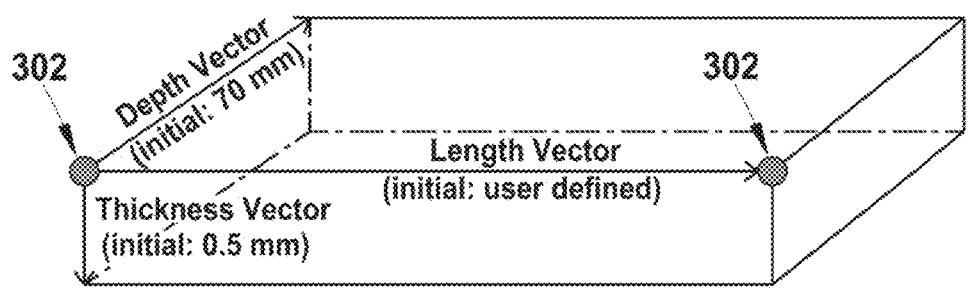
FIG. 3 illustrates an example hexahedron that is formed between two adjacent digitized landmarks during a virtual osteotomy according to implementations described herein.

The virtual knife is a group of multi-connected hexahedrons formed from a set of manually digitized landmarks. For example, as shown in FIG. 2, digitized dots 202 generate the user-defined cutting plane on the composite 3D model 200. These digitized landmarks determine the initial orientation and length of each hexahedron. An example hexahedron between adjacent digitized dots is shown in FIG. 3. To form the top face of the hexahedron, a pair of adjacent digitized landmarks 302 are copied and perpendicularly extended 70 mm "into" the screen (i.e., depth vector in FIG. 3). The distance between digitized landmarks 302 is the length vector in FIG. 3. The length vector between digitized landmarks 302 is defined by the user. To form the bottom face of the hexahedron, the four landmarks for the upper face are copied and extended vertically 0.5 mm (i.e., thickness vector in FIG. 3). Using these default dimensions, a hexahedron is formed between each pair of adjacent landmarks. Thus each landmark is used twice for adjacent hexahedrons, except at the beginning and the end.

Figure 4:
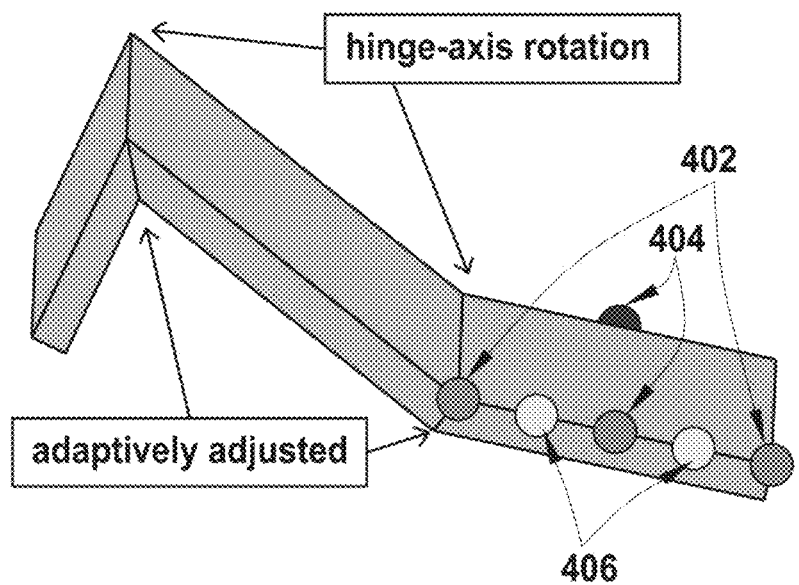
FIG. 4 illustrates hinge-axis joints that combine the top faces of the hexahedrons, while the bottom faces are adaptively adjusted during a virtual osteotomy, according to implementations described herein.

The next step is to chain all the hexahedrons together to form a "curved" virtual knife based on the digitized landmarks. If adjacent vertical faces of the hexahedrons are parallel (threshold: <$1.0e^{-9}$), the two adjacent hexahedrons are combined into a single hexahedron. Otherwise, the two top faces of the hexahedrons are joined together by a hinge-axis joint, and two bottom faces are adaptively adjusted, either longer or shorter, depending on the direction of the angle. An example hinge-axis joint is shown in FIG. 4. Finally, six control spheres are added to each hexahedron, allowing for manual adjustment of the length and orientation. Spheres 402 at each end of the hexahedron control the length of the hexahedron. Spheres 404 on each side of the hexahedron control the width of the knife. Spheres 406 adjust angle between adjacent hexahedrons. A control panel is also available to translate, rotate, or adjust the thickness of the entire virtual knife.

Cut the 3D Bone Model into Two Bony Segments

The cutting and separation of a 3D bone model into two bony segments is completed through triangle classification, "broken" triangle reconstruction, and capping the cutting surface. This process is described below in detail.

Classify Triangles that Intersect with the Multi-Connected Hexahedrons

Figure 5:
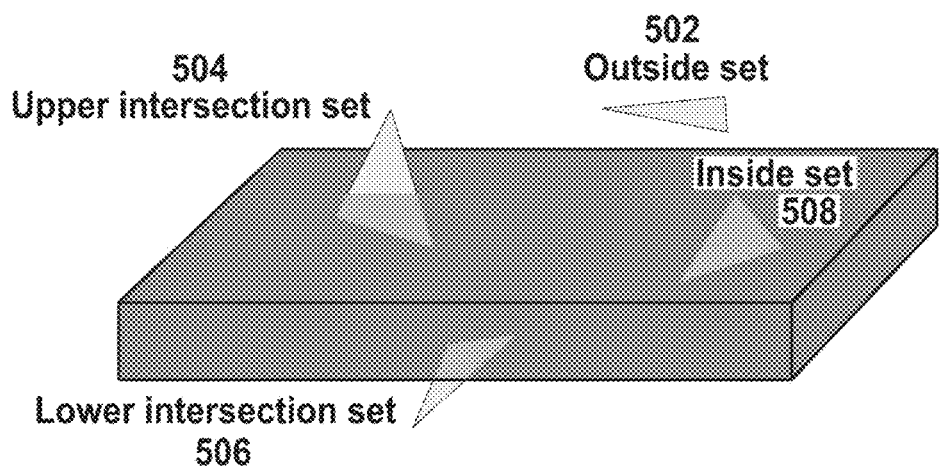
FIG. 5 illustrates different relationships between a triangle and the hexahedron during a virtual osteotomy according to implementations described herein.

The number of triangles in a 3D surface model is often excessive (e.g., 3 million). This is especially true on the models generated from CBCT scans. Therefore, a two-step coarse-to-fine algorithm was developed to efficiently classify all the triangles into four sets based on their relationship with the hexahedron knife. They are: outside set (no intersection) 502, upper intersection set (intersection with the top face) 504, lower intersection set (intersection with the bottom face) 506, and inside set (completely inside the hexahedron) 508 as shown in FIG. 5.

The first step is to coarsely classify triangles into the outside set at the triangle level using a subdivision classification algorithm. The bounding box of a selected bone model is first divided into 64 evenly spaced elements that are used as basic units. A mesh collision detection algorithm [30] is then used to identify and mark all the elements that are outside of the virtual hexahedron knife. Afterward, the bounding box of each triangle in the bone model is mapped to its corresponding elements. If all the elements mapped by the triangle bounding box are "outside", then this triangle is also classified as "outside". No further calculation will be performed on this triangle.

After most of the "outside" triangles have been identified by coarse classification, the next step is to finely classify the remaining triangles at the vertex level. Each triangle has three vertices ($v_1$, $v_2$, and $v_3$), and each vertex's relationship to the hexahedron knife is defined using Eqn. (1) below.

$$I(v, f_j) = \begin{cases} +1 & \text{above the plane} \\ 0 & \text{on the plane} \\ -1 & \text{below the plane} \end{cases}, \text{ for } j = 1, 2, 3, \ldots, 6 \quad (1)$$

where $I(v, f_j) = \text{Sign}(a_j x + b_j y + c_j z + d_j)$ indicates the relationship between $v$ and $f_j$, and $v=(x, y, z)$ represents the vertex of a given triangle; $f_j = a_j x + b_j y + c_j z + d_j$ represents one of the six plane functions of the hexahedron; a, b, c are three components of the normal vector of the plane j that points "out" of the hexahedron; and d is the offset of the plane from the origin of the global reference frame. If the solution of I(v,f$_j$) is "−1", the vertex is classified as "inside" the hexahedron. If the solution is "0", the vertex is classified as "on" the hexahedron. Otherwise, the vertex is classified as "outside" the hexahedron. If a triangle has vertices related to multiple hexahedrons, then the triangle and its three adjacent neighbors are further divided into smaller triangles. This computation iterates until each triangle is related to only one hexahedron. Based on these rules, each triangle can now be classified as "outside", "upper intersection", "lower intersection", or "inside" at the vertex level. At this point, all inside triangles are discarded (deleted), because they are inside the hexahedron knife. Only the upper and lower intersection triangles are further processed in the next step.

Create New Triangles to Replace the "Broken" Triangles

Figure 6:
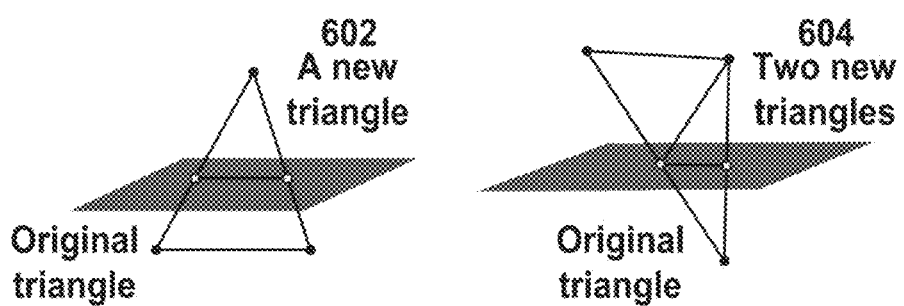
FIG. 6 illustrates how broken triangles are fixed depending on the number of vertices still outside of the plane during a virtual osteotomy according to implementations described herein.

The virtual knife will cut through all the upper and lower intersection triangles, resulting in "broken" triangles with two intersection points on each side of the triangle. "Broken" triangles are fixed based on the number of vertices that remain "outside" of the hexahedron. As shown in FIG. 6, if only one vertex is outside of the hexahedron (left side of FIG. 6), a new triangle 602 is constructed using the vertex and the two intersection points. If two vertices of a triangle are outside the hexahedron (right side of FIG. 6), then two new triangles 604 are constructed. Using this algorithm, the original "broken" triangles are replaced with new "intact" triangles.

Separate the Osteotomized Model into Two New Bony Segments

Figure 12:
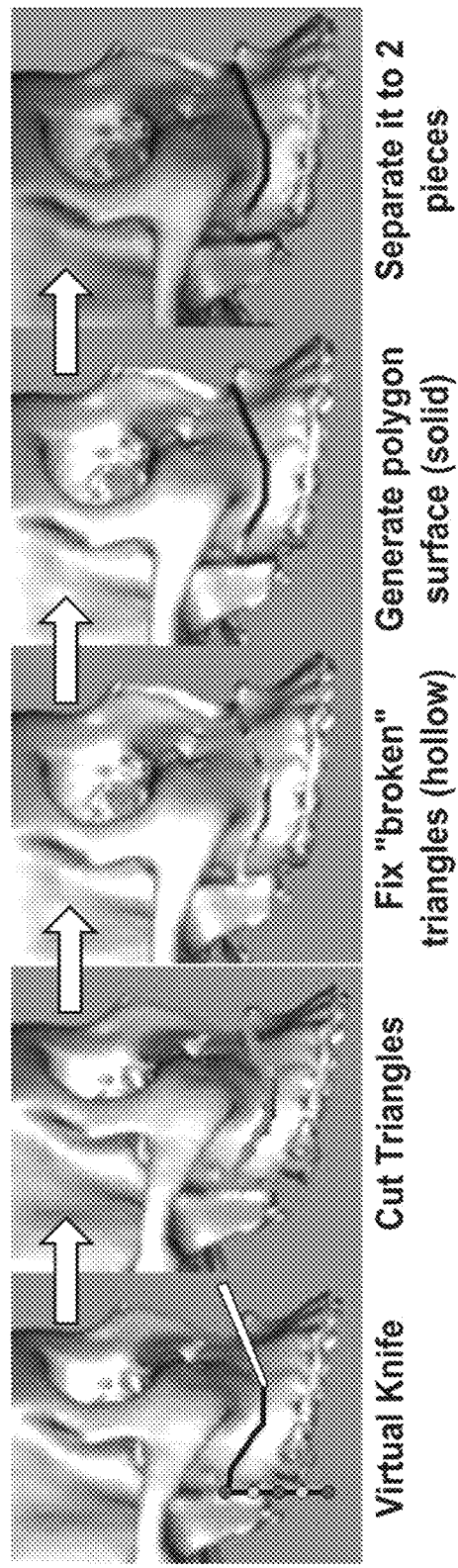
FIG. 12 illustrates the process for performing a virtual osteotomy on an example composite 3D module according to implementations described herein.

Since the 3D models are created by surface reconstruction, the cutting surface of osteotomized segments are open. Therefore, triangulated polygon surfaces are created to "cap" their corresponding segments as shown in FIG. 6. To generate the cap, all intersecting edges between the bony model and the hexahedron surface are contoured. Next, a new surface is reconstructed by reorganizing, simplifying, and triangulating each contour. Afterward, all the outside, upper intersection, lower intersection triangles, and the cap for each segment are combined to form a temporary bone model. Finally, using the 3D region growing method, the temporary bone model is separated into the two osteotomized bony segments. FIG. 12 illustrates the process for performing the virtual osteotomy on the composite 3D model from generating the "virtual knife" through separating the osteotomized bony segments.

Module 5: Surgical Simulation

Figure 7A:
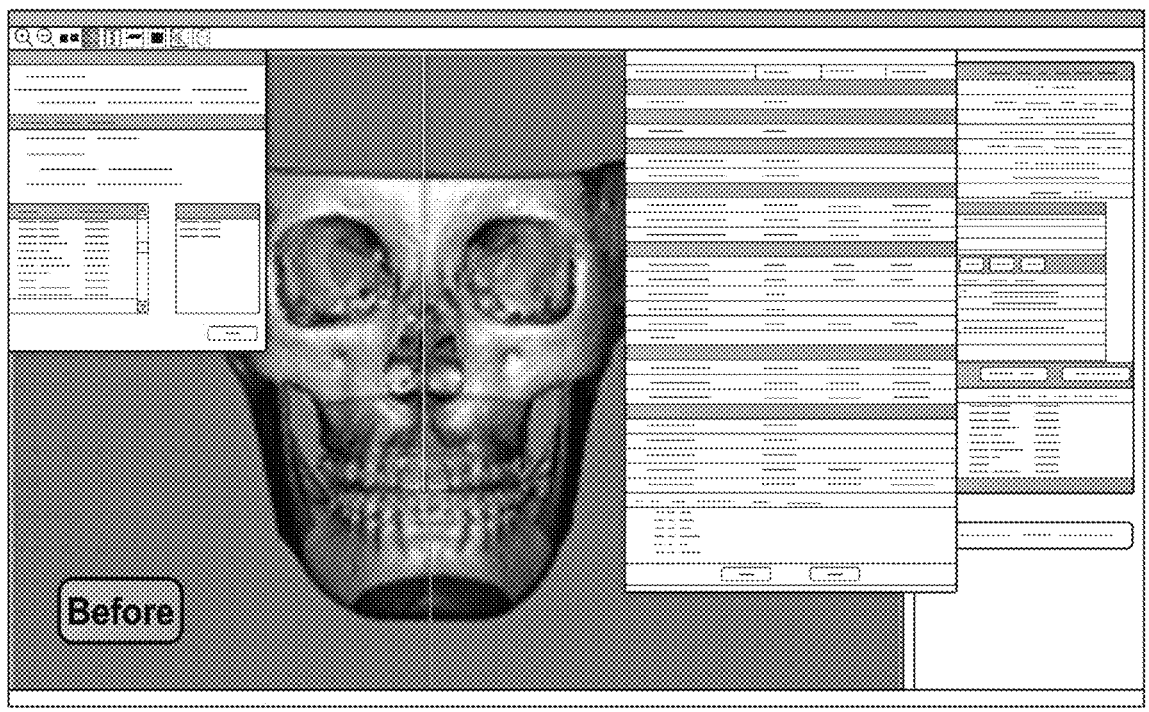
FIGS. 7A and 7B illustrate before and after views of a virtually simulated example orthognathic surgery: Le Fort I osteotomy, bilateral sagittal splint osteotomy and genioplasty.
Figure 7B:
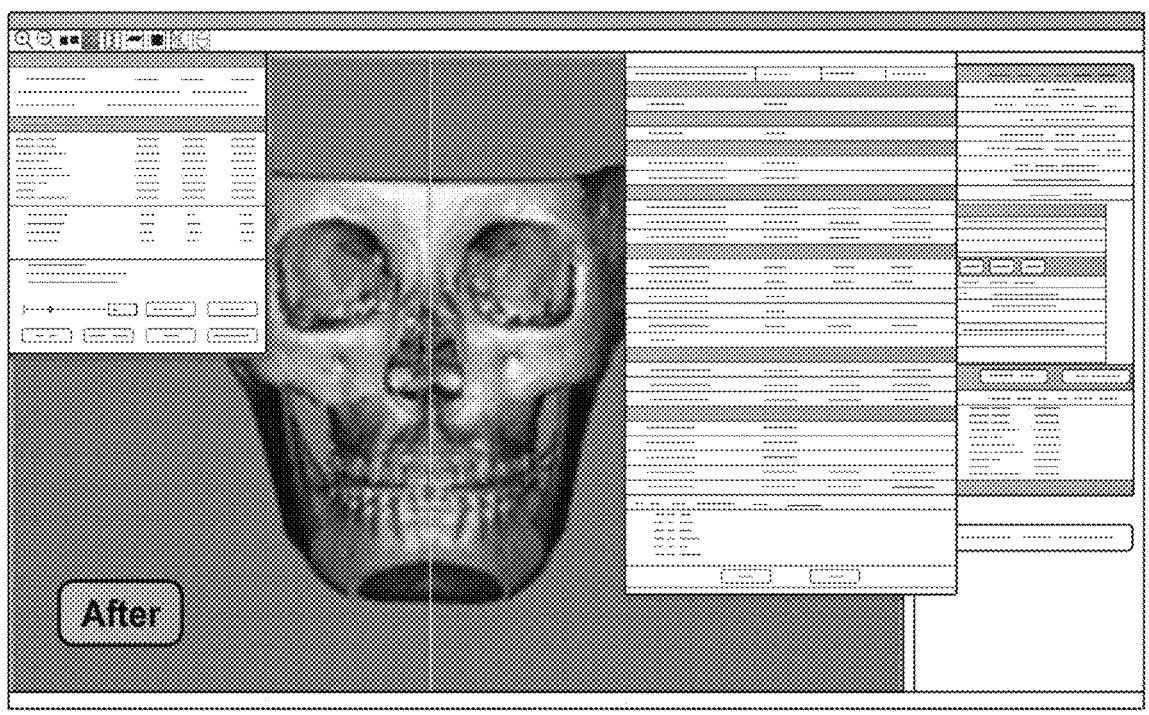

Once the osteotomies are performed, users (e.g., doctors or surgeons) can simulate the desired orthognathic surgical procedure in the Surgical Simulation module 110. There are three main steps in surgical simulation: (1) establishing a final dental occlusion between the upper and lower teeth, (2) simulating a maxillary and a mandibular surgery by moving the related bony segments to a desired position, and (3) simulating a genioplasty if necessary [4]. During the surgical simulation, all the 3D cephalometric measurements are updated in real-time, following the movements of the bony segments. The 3D cephalometric measurements are displayed on a display device as shown in FIG. 7B. The prerequisite for any surgical simulation is all the required bony segments for a surgery must exist, and their associated anatomical landmarks must be digitized. As described above, AnatomicAligner automatically establishes a customizable hierarchical structure for these bony segments, before the start of surgical simulation as shown in FIG. 7A.

The first step of surgical simulation is to establish final dental occlusion. This is to restore the patient's malocclusion to a normal occlusion. The final occlusion at maximum intercuspation (MI) is to be determined by surgeons on a set of stone dental models, prior to the surgical simulation [1,2,31,32]. The articulated stone dental models at MI are then scanned into the computer using a high-resolution laser or CBCT scanner, creating the final occlusal template [4]. Using this template, the lower teeth and its "child", the mandibular distal segment, are placed to MI with the corresponding upper teeth of the maxillary Le Fort I segment. This is the desired relation between the maxilla and the mandible. However, this is only a temporary position, where only the desired relationship between the mandibular distal segment and the maxillary Le Fort I segment is established. In the following steps of surgical simulation, this relation is maintained by grouping the maxillary Le Fort I and the mandibular distal segments into the maxillomandibular combination.

The second step is to move all bony segments, including the maxillomandibular combination, into their final desired positions. Each segment can be moved and rotated in six-degree of freedom. The first surgical corrections (translation and rotation) are made to the maxillomandibular combination, usually around the maxillary dental midline point. Following the clinical protocol, surgical corrections are then performed in a specific sequence: midline correction (mediolateral correction), yaw correction, roll correction, vertical position adjustment, pitch adjustment, and finally anteroposterior position adjustment [4]. Afterward, the right and left proximal segments are aligned to the mandibular distal segment by rotating them around their center of rotation, located in the centers of their corresponding mandibular condyles.

The last step in surgical planning is to simulate a genioplasty. This step is optional. Its necessity is based on the doctor's clinical judgement. The chin segment can be osteotomized either before or after the maxillomandibular combination is moved into the desired position. The chin segment is moved and rotated in six-degree of freedom around an anatomic landmark, the pogonion, which is located at the chin point.

Finally, the initial and final position of each bony segment can be visualized and compared using a "position review" function. A before and after view of a patient's surgical simulation can be seen in FIGS. 7A and 7B, respectively.

Module 6: Surgical Splint/Template

The Surgical Splint/Template module 112 is used to design surgical splints or templates, which are used to transfer the computerized surgical plan to the patient at the time of the surgery. The surgical splint is a horseshoe-shaped teeth-anchored wafer that is placed between the upper and lower teeth. In a double-jaw surgical procedure, unlike the procedure seen in surgical simulation, the maxilla and the mandible are always osteotomized separately. One jaw is always osteotomized first and moved to the desired position, while the other jaw remains intact. Once the first jaw is in position, the other jaw is then osteotomized and moved to the desired position. Therefore, double jaw surgeries require two splints: an intermediate and final splint. An intermediate splint is used to move the first osteotomized jaw to the desired position in relation to the intact opposite jaw. A final splint is used to position the second osteotomized jaw in relation to the first jaw. A surgeon decides which jaw to operate on first based on the clinical assessment, because different clinical indicators dictate maxillary or mandibular surgery first. However in a single-jaw surgery, only one jaw is osteotomized and moved to the final desired position in relation to the intact jaw. Therefore, only a final splint is required. The procedure of designing a surgical splint is described below in details.

Select the Type of Splint to be Designed

There are three possible types of surgical templates: an intermediate splint for maxillary surgery first, an intermediate splint for mandibular surgery first, and a final splint. Once the type of splint is selected, the upper and lower dental arches are automatically moved to the correct position for the intended type of surgery. For maxillary surgery first, the upper dental arch is displayed at its final position, while the lower dental arch is at its original position. The opposite is true for mandibular surgery first. For the final splint, both dental arches are displayed at their final positions.

Autorotate the Lower Dental Arch (Optional)

When using an intermediate splint, only one jaw is moved to its final position, while the other intact jaw remains at its original position. This may cause collisions between the upper and lower teeth. To avoid this problem, the lower teeth needs to be autorotated around the center of rotation of the right and left condyles. The same rotation is also performed clinically at the time of the surgery. However, autorotation is usually not required for the final splint.

Design the Horse-Shoe Shaped Raw Model of the Splint

Figure 8A:
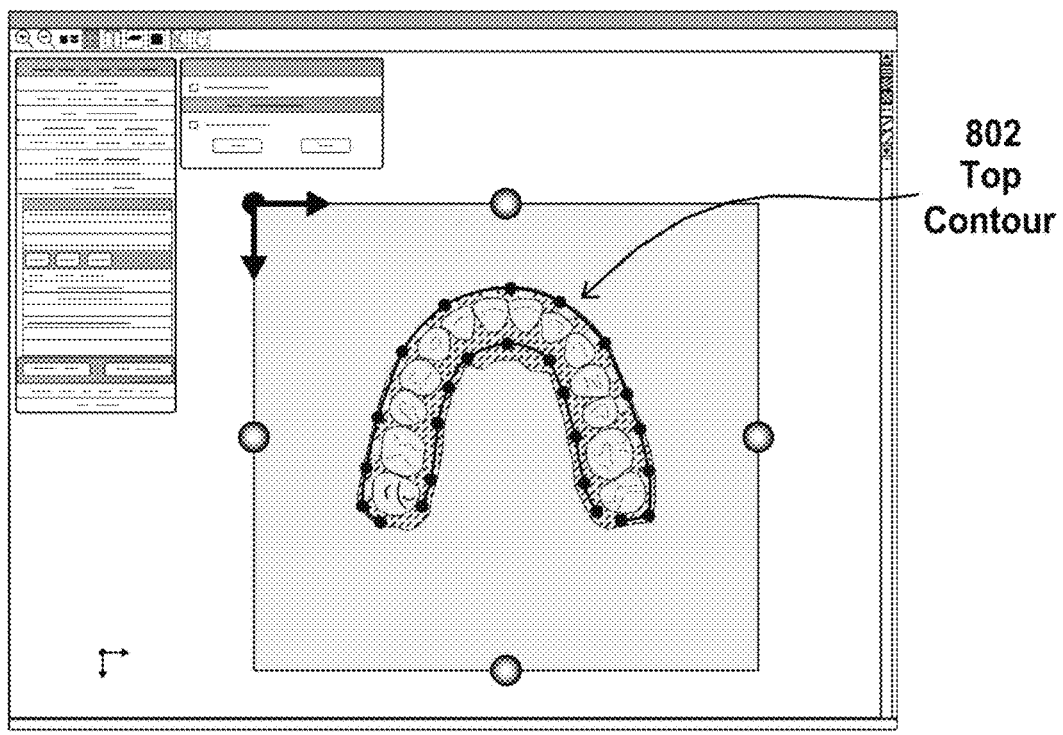
FIGS. 8A and 8B illustrate surgical splint design according to implementations described herein.

The first step is to digitize three landmarks on the occlusal surface of the upper dental arch to form a top plane for the splint. This plane is automatically offset 2 mm away from the occlusal surface to create enough anchorage (thickness) for the splint. The next step is to create a top contour 802 for the top face of the splint by manually tracing the upper dental arch onto top plane using a cardinal spline as shown in FIG. 8A.

The bottom plane of the splint, for the lower dental arch, is created using the same steps as the top plane. The top contour 802 is then copied to the bottom plane, forming the bottom contour 804, for the bottom face of the splint. It can then be manually edited to fit the lower dental arch. This is to ensure that both top and bottom contours have the same number of points.

If needed, a top and bottom contour extensions 802a, 804a can also be created by copying the corresponding contours and moving them 0.5 mm towards the occlusal surface. The contour extensions 802a, 804a serve as transitional layers between the top and bottom face, in case there is a large positional discrepancy between the upper and lower teeth. This is common when designing the intermediate splint.

Figure 8B:
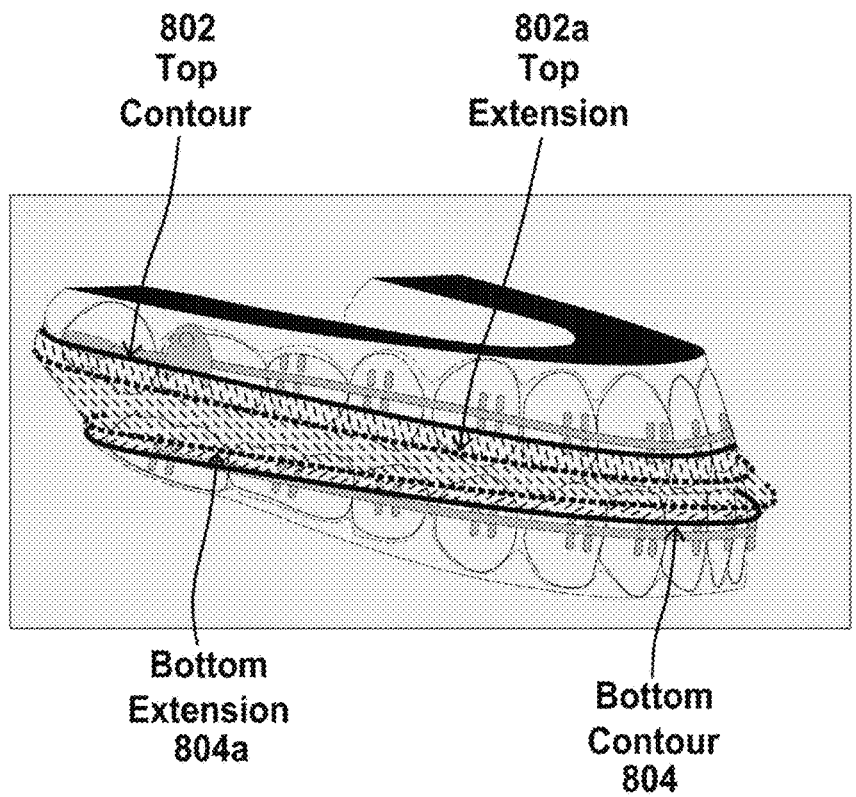

Collisions between contours are automatically detected to ensure the quality of the raw splint models. Each contour and its extension can be adjusted individually to avoid the collisions. Finally, corresponding points of each contour are automatically connected and triangulated, forming a surface model of the raw splint as shown in FIG. 8B.

Create the Final Model of the Splint

Figure 9A:
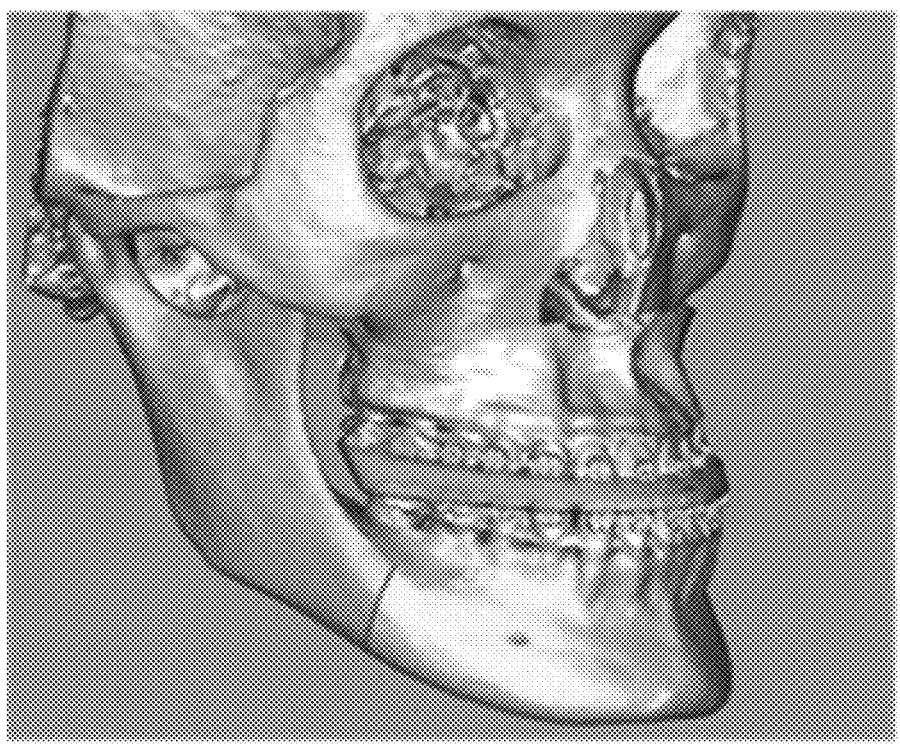
FIG. 9A illustrates an example computerized intermediate model with a reconstructed bone models. The first osteotomized jaw is moved into its desired final position, while the other jaw remains intact.
Figure 9B:
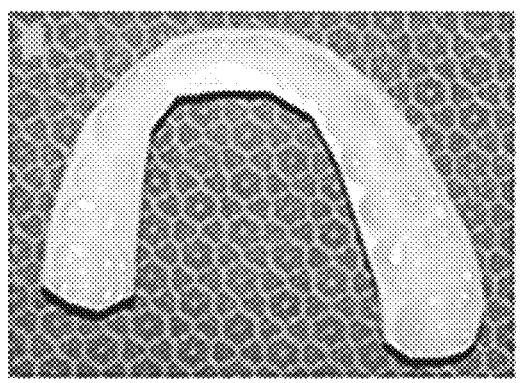
FIG. 9B illustrates how the computerized splint can be printed using a 3D printer.
Figure 9C:
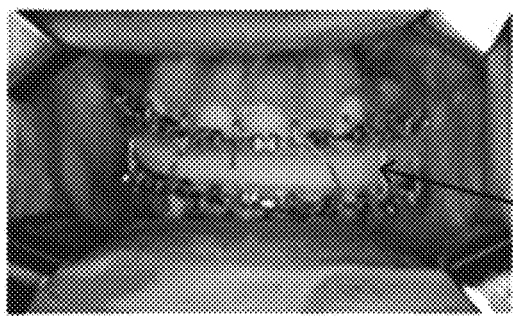
FIG. 9C illustrates use of the surgical splint to transfer the digital surgical plan to the patient at the time of surgery.

The final model of the splint is generated by Boolean operation. It subtracts the upper and lower teeth from the raw splint model. The final model of the splint is exported as computer-aided design (CAD) file such as an .stl file, for example, and printed using any 3D printer that uses US Food and Drug Administration (FDA) approved biocompatible material. An example splint formed of biocompatible material is shown in FIG. 9B. The 3D printed splint 902 is now ready to be used in the operating room during an orthognathic procedure as shown in FIG. 9C.

Two evaluations have been completed to examine the accuracy of the AnatomicAligner system described above. In the first retrospective study, the accuracy of 3D models generated using the AnatomicAligner system was evaluated. In the second prospective study, the splints designed by the AnatomicAligner system were evaluated.

Validation #1

Patients and Methods

For the first validation, CT datasets of 30 historical patients were randomly selected from our digital patient archives using a random number table. These patients were diagnosed with dentofacial deformities and had underwent double-jaw orthognathic surgery. The accuracy of AnatomicAligner system was evaluated and compared to the industry gold standard, MATERIALISE MIMICS 17.0 (Materialise NV, Leuven, Belgium), in the following areas: 1) CT model reconstruction, 2) virtual osteotomy, and 3) translational and rotational movements. It should be understood that currently available commercial software such as the MATERIALISE MIMICS system is not capable of transferring recorded NHP to 3D models and/or performing true 3D cephalometric analysis as described above. Therefore, some of the functions in AnatomicAligner, e.g., NHP and 3D cephalometry, could not be evaluated against the MATERIALISE MIMICS system.

To evaluate the accuracy of CT model reconstruction, the DICOM dataset of the same patient were imported into both systems. The masks of the skeletal structure of the head were initially created using a predetermined threshold (grayscale: 1250). Then, both masks were manually edited to remove the spine by removing the spine mask on the same sequential axial slice. Finally, using region growing in each system, masks of the skull were created. The 3D skull models were reconstructed in high resolution (sampling 2:2:1 in x,y,z) using Marching Cubes algorithm in AnatomicAligner and a proprietary algorithm in the MATERIALISE MIMICS system. To compare the two models, RapidForm software (INUS Technology, Korea) was used to compute the surface deviation between the two models. Surface deviation between the two models was calculated as the absolute mean Euclidean distance. Both the mean and standard deviation (SD) were recorded. Since the origins of the coordinate systems were different between the two systems, the MATERIALISE MIMICS system model was registered (translation only) to the AnatomicAligner model, in Rapid Form.

To evaluate the accuracy of virtual osteotomy, osteotomized segments generated by both systems were compared. In order to avoid confounding errors that might be the result of segmentation and 3D reconstruction, a single midface model, generated in the AnatomicAligner, was imported into both systems. A Le Fort I osteotomy was then performed in both systems following the clinical standard. In the AnatomicAligner, the cut was made using the "virtual osteotomy" function, whereas the "PolyPlane" function was used in the MATERIALISE MIMICS system. Two bony segments were generated in each system: a Le Fort I segment and the remaining of the midface segment. The surface deviation for both Le Fort I and the remaining midface segments generated by the two systems were calculated in RapidForm.

Finally, to evaluate the accuracy of translational and rotational movements, the surface deviation was calculated between the 3D models of the two systems after a specific transformation matrix was applied. The Le Fort I segment generated by the AnatomicAligner for comparing virtual osteotomy was used in both systems. This is done to avoid confounding errors from 3D reconstruction and/or virtual osteotomy. Once the Le Fort I segment had been imported into both systems, it was duplicated. The first Le Fort I segment was translated 4 mm along the x axis, 6 mm along the y axis, and 8 mm along the z axis. The second Le Fort I segment was rotated 6° around the x axis, 8° around the y axis, and 10° around the z axis. The two Le Fort I segments were once again imported into RapidForm and surface deviation between the corresponding models was calculated.

Validation Results

Figure 10:
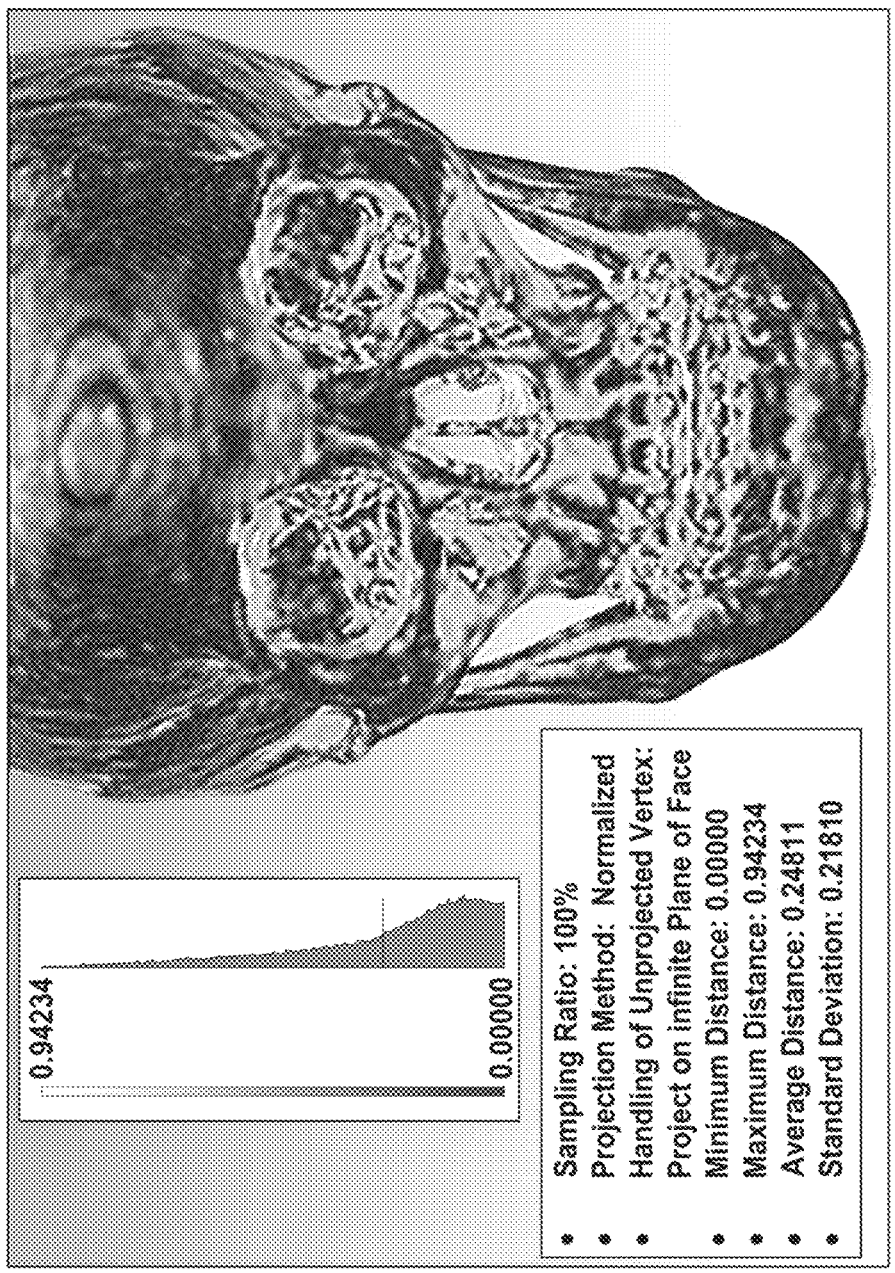
FIG. 10 illustrates average surface deviation between the AnatomicAligner and the MATERIALISE MIMICS system models after segmentation and 3D model reconstruction.

The average surface deviation between the two models after 3D model reconstruction in the MATERIALISE MIMICS system and AnatomicAligner was 0.3 mm with a SD of 0.03 mm. These errors were mainly attributed to scattering at the margins of the image, where the images exceeded field of view during CT acquisition, thin bones in the nasal cavity and orbital frames, and artifacts caused by amalgam and orthodontic bands as shown in FIG. 10. Once these errors were removed, the average surface deviation was reduced to less than 0.2 mm. These error margins are clinically insignificant.

Furthermore, the results of the virtual osteotomy comparison showed an average surface deviation of 0.001 mm between the two Le Fort I segments with a SD of 0.001 mm. The results of the translation comparison showed an average surface deviation of 0.001 mm with a SD of 0.001 mm between the two Le Fort I segments. And finally, the results of the rotational comparison showed an average surface deviation of 0.01 mm with a SD of 0.01 mm.

Validation #2

Patients and Methods

The purpose of this prospective validation was to determine if the planned results, using the AnatomicAligner system, were at least as good as the current gold standard (designed and printed by commercial services). Ten consecutive patients were included based on the following criteria: 1) patients who were diagnosed with a dentofacial deformity; 2) patients who were scheduled for double-jaw surgery; and 3) patients who had CT scans as a part of their diagnosis and treatment. For each patient, the orthognathic surgery was planned by a single surgeon (J. G.) in conjunction with a commercial service provider (3D Systems— Medical Modeling, Golden, CO) following the CASS protocol [3,4]. Surgical splints (called commercial splints in this study) were designed and printed by the commercial service provider, and these splints were used at the time of surgery. The same surgeon then repeated the same surgical planning using the AnatomicAligner system, from importing the DICOM images to designing the surgical splints. The transformation matrix used by the service provider was then duplicated in the AnatomicAligner system and applied to each bony segment. Finally, the intermediate splint designed in the AnatomicAligner, called the AnatomicAligner splint, was printed by a 3D printer (Object30 Orthodesk, Stratasys Ltd, Eden Prairie, Minn.) using FDA approved MED610 material. Only the intermediate splint was evaluated. This is because the position of the intermediate splint is directly determined by the system, unlike the final splints. Therefore, the accuracy of the intermediate splint is the most direct benchmark for measuring the accuracy of the system.

The fitting of the printed commercial and AnatomicAligner splints were evaluated by two oral surgeons who are experienced in orthognathic surgery (H. M. and D. H.). Neither were involved in the surgical planning or splint printing process. The evaluators were also blinded from each other's evaluation results. However, since the materials used to print splint by lab (i.e., AnatomicAligner splint) and the commercial service were different, it was impossible to blind the evaluators from the system used to design the splint. Therefore, the following strategy was used to prevent conformation bias. For each patient, the commercial splint was used to mount the upper and lower stone dental models onto a Galetti dental articulator. Afterward, the commercial splint was removed, and the AnatomicAligner splint was inserted for the evaluation. The evaluators were then asked to evaluate the fitting of the splint based on the clinical standard. The most important aspect was to determine whether the AnatomicAligner splint could correctly establish the desired intermediate occlusion between the upper and lower teeth. To do this, the fitting of the AnatomicAligner splint was evaluated while both the upper and lower stone models were mounted on the Galetti dental articulator, a relationship that was predetermined by the commercial splint. Then the rocking and shifting on the individual upper and lower dental models were evaluated individually. Three ranks were given for each splint in each respect: Rank #1 represented perfect fit, Rank #2 represented a partial fit (mild shifting or rocking), and Rank #3 represented no fit at all. Finally, the ranking scores determined by the two evaluators were paired and summarized descriptively.

Validation Results

The evaluation results showed that all the AnatomicAligner splints fit perfectly (Rank #1) while the models were mounted in the intermediate occlusion on a Galetti dental articulator. In addition, all the AnatomicAligner splints were seated perfectly on the stone models, without any rocking (Rank #1) or shifting (Rank #1) while they were evaluated individually on the upper and lower models.

A CASS system, the AnatomicAligner, for planning orthognathic surgery was developed as described above. The AnatomicAligner system allows doctors to accurately plan orthognathic surgery following a streamlined clinical protocol [4]. In addition, the true 3D cephalometric analysis [16], including the five geometric properties of orientation, symmetry, position, size and shape, is implemented in a surgical planning system for the first time. This is especially important for correctly quantifying deformities and planning treatment. Finally, the surgical splints can be effectively designed in the system and printed by any in-house 3D printer that uses FDA-approved biocompatible materials. These splints are used at the time of the surgery to accurately transfer the computerized surgical plan to the patient.

The AnatomicAligner system also allows the following: 1) The user-interface of the system is designed with the perception that end users are medical doctors with little knowledge in computer graphics. Necessary prompts and error-checks are also implemented to guide and warn the users. 2) A versatile and efficient virtual osteotomy is implemented, so doctors can freely design and modify any type of osteotomy. A two-step coarse-to-fine triangle classification algorithm is developed to significantly improve the efficiency of virtual osteotomy. 3) During the registration and surgical simulation, all involved bony segments are moved and rotated under an automatically generated hierarchical structure. 4) The design of surgical splint is a guided semi-automatic procedure.

It should be appreciated that the logical operations described herein with respect to the various figures may be implemented (1) as a sequence of computer implemented acts or program modules (i.e., software) running on a computing device (e.g., the computing device described in FIG. 11), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 11, an example computing device 1100 upon which embodiments of the invention may be implemented is illustrated. It should be understood that the example computing device 1100 is only one example of a suitable computing environment upon which embodiments of the invention may be implemented. Optionally, the computing device 1100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 1100 typically includes at least one processing unit 1106 and system memory 1104. Depending on the exact configuration and type of computing device, system memory 1104 may be volatile (such as random access memory (RAM)), non-volatile (such as read-only memory (ROM), flash memory, etc.), or some combination of the two. This most basic configuration is illustrated in FIG. 11 by dashed line 1102. The processing unit 1106 may be a standard programmable processor that performs arithmetic and logic operations necessary for operation of the computing device 1100. The computing device 1100 may also include a bus or other communication mechanism for communicating information among various components of the computing device 1100.

Computing device 1100 may have additional features/functionality. For example, computing device 1100 may include additional storage such as removable storage 1108 and non-removable storage 1110 including, but not limited to, magnetic or optical disks or tapes. Computing device 1100 may also contain network connection(s) 1116 that allow the device to communicate with other devices. Computing device 1100 may also have input device(s) 1114 such as a keyboard, mouse, touch screen, etc. Output device(s) 1112 such as a display, speakers, printer, etc. may also be included. The additional devices may be connected to the bus in order to facilitate communication of data among the components of the computing device 1100. All these devices are well known in the art and need not be discussed at length here.

The processing unit 1106 may be configured to execute program code encoded in tangible, computer-readable media. Tangible, computer-readable media refers to any media that is capable of providing data that causes the computing device 1100 (i.e., a machine) to operate in a particular fashion. Various computer-readable media may be utilized to provide instructions to the processing unit 1106 for execution. Example tangible, computer-readable media may include, but is not limited to, volatile media, non-volatile media, removable media and non-removable media implemented in any method or technology for storage of information such as computer readable instructions, data structures, program modules or other data. System memory 1104, removable storage 1108, and non-removable storage 1110 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1106 may execute program code stored in the system memory 1104. For example, the bus may carry data to the system memory 1104, from which the processing unit 1106 receives and executes instructions. The data received by the system memory 1104 may optionally be stored on the removable storage 1108 or the non-removable storage 1110 before or after execution by the processing unit 1106.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Defining a Primal Reference Frame

Techniques for defining a primal reference frame are described below. As described above, the orthognathic surgical planning system and/or AnatomicAligner (as part of Module 2) can define the primal reference frame, which occurs before performing a 3D cephalometric analysis. In other words, a frame of reference is needed to quantify a geometric property of the composite 3D model. For example, like a builder uses string and level to set a construction line, a surgeon needs reference planes to reconstruct a face. The face, being a 3D structure, needs three planes of reference: vertical (sagittal), horizontal (axial), and transverse (coronal). The vertical plane divides the face into right and left halves and together with the transverse plane, helps in defining symmetry. The horizontal plane determines the forward or backward tilt of the face and guides the surgeon to the correct forward placement of any facial feature. Correctly establishing the anatomical reference frame is important. When the face is symmetric, establishing a reference frame may be easy, but when the face is skewed, establishing a reference frame is much more difficult.

To establish a reference frame, an algorithm that automatically calculates the plane of symmetry for any face (or composite 3D model thereof), even if it is skewed, can be used. The algorithm uses facial landmarks including, but not limited to, the corner of the eyes, tip of the nose, middle of the chin, and ear canals. This disclosure contemplates that landmarks other than those provided as examples can be used. In a first step, the algorithm collects facial landmarks (e.g., about 50 landmarks) and creates a cloud of points. Next, the cloud of points is copied and flipped, making a mirror image. Then, using a number of iterations, the algorithm translates and rotates the mirror image until it is fitted to the original. At each iteration, the algorithm learns to ignore the most skewed portions of the face (or composite 3D model thereof), giving more value to the most symmetric anatomy. Finally, after the fitting is completed, the algorithm joins the original and the flipped landmarks in a single group and calculates the plane (e.g., sagittal, axial, or coronal) that best divides the right and left landmarks. The result is the best possible plane of symmetry.

An example method for establishing a primal reference frame is provided in Gateno, J. et al., The primal sagittal plane of the head: a new concept, Int J Oral Maxillofac Surg, 45 (3):399-405 (2016), the disclosure of which is incorporated by reference in its entirety. Alternatively or additionally, the primal reference frame can be established using the technique as described below with regard to FIG. 13, which includes calculating weighted Procrustes distances. This disclosure contemplates that the primal reference frame for the 3D model can be determined, for example, using a computing device such as the computing device 1100 shown in FIG. 11. The example method can include the following steps: (1) identifying a plurality of landmarks on the 3D model, where the landmarks define a cloud of points; (2) creating a mirror-image copy of the cloud of points; (3) iteratively translating and/or rotating the mirror-image copy until fitted with the cloud of points; (4) superimposing the mirror-image copy and the cloud of points to create a single group of points; and (5) calculating a plane of symmetry dividing the single group of points. It should be understood that the plane of symmetry can be a midsagittal plane, an axial plane, or a coronal plane of the 3D model.

Figure 13:
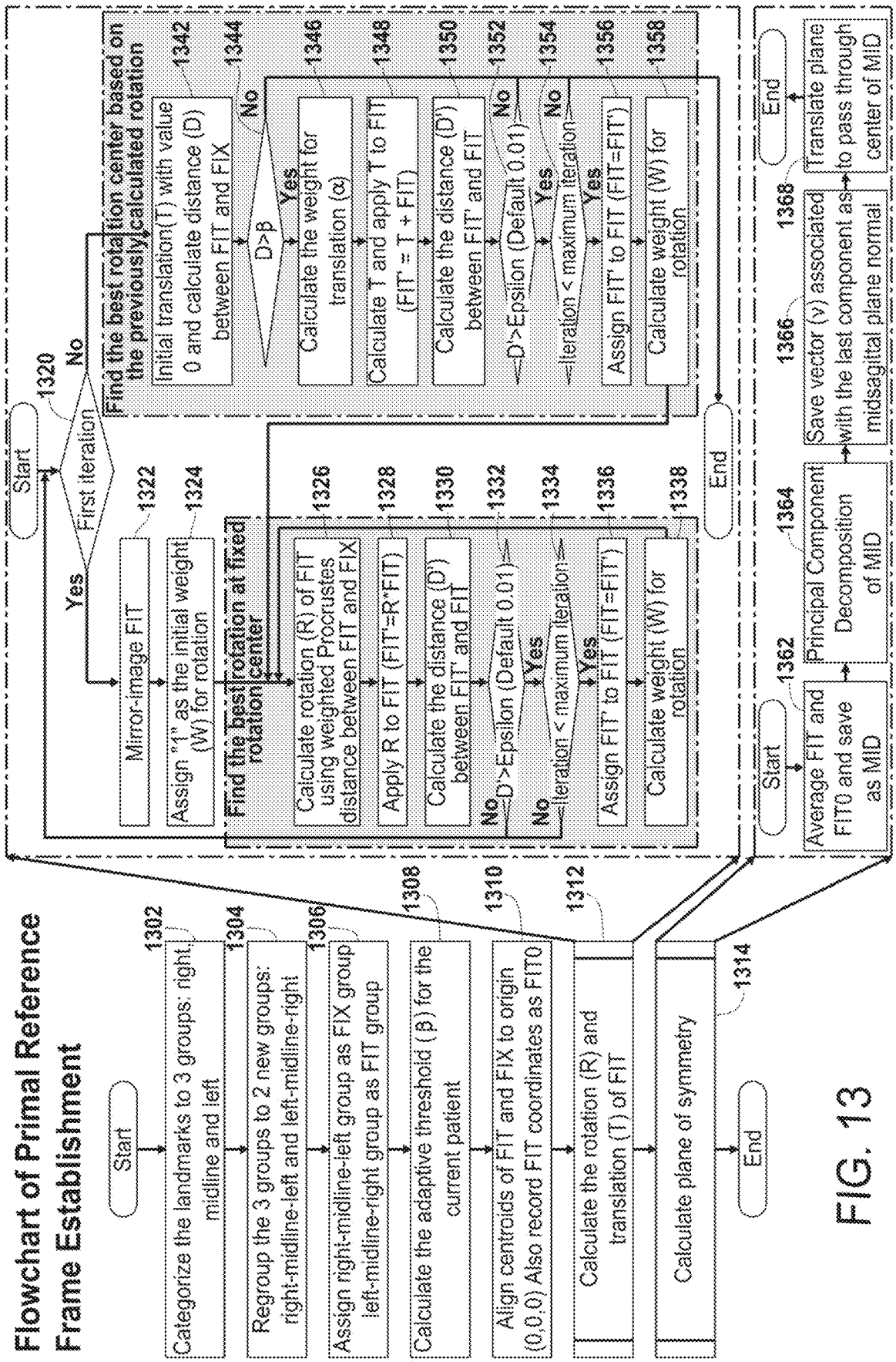
FIG. 13 is a flowchart illustrating example operations for defining a primal reference frame according to an implementation described herein.

With reference to FIG. 13, example operations for determining a primal reference frame for a three-dimensional (3D) model (e.g., the composite 3D model described above) are shown. FIG. 13 is specific to determining the midsagittal plane of the composite 3D model described herein. It should be understood that the example operations can be used to determine the midsagittal plane, the axial plane, or the coronal plane of the composite 3D model described herein. This disclosure contemplates that the example operations shown in FIG. 13 can be performed, for example, using a computing device such as the computing device 1100 shown in FIG. 11.

At 1302, a plurality of landmarks are categorized into three groups: right, midline, and left. At 1304, the three groups of landmarks are regrouped into two groups: right-midline-left and left-midline-right. At 1306, the right-midline-left group is assigned as "FIX", and the left-midline-right group is assigned as "FIT". At 1308, an adaptive threshold (β) for the subject (i.e., patient specific) is calculated. At 1310, centroids of FIT and FIX are aligned to the origin (0, 0, 0) and FIT coordinates are stored (e.g., in memory) as "FIT0". At 1312, rotation (R) and translation (T) of FIT are calculated. At 1314, the plane of symmetry (e.g., midsagittal plane) is calculated. At 1315, the primal reference frame is calculated based on the midsagittal plane and the same groups of the landmarks, and operations proceed to END (i.e., step 1315 is complete).

Sub-operations for step 1312 are provided below. At 1320, for the first iteration, operations proceed to step 1322. These operations find the best rotation (R) at fixed rotation center. For subsequent iterations, operations instead proceed to step 1342. These operations find the best rotation center based on the previously determined rotation (R). For the first iteration, at 1322, a mirror image copy of FIT is created. The left-midline-right group (i.e., FIT) is mirror-imaged in the example shown in FIG. 13. This disclosure contemplates that the right-midline-left group (i.e., FIX) can optionally be mirror imaged in other implementations and operations adjusted accordingly. At 1324, the initial weight (W) for rotation (R) is assigned as "1". At 1326, rotation (R) of FIT is calculated using a weighted Procrustes distance between FIT and FIX. At 1328, rotation (R) is applied to FIT to obtain FIT' (i.e., FIT'=R*FIT). At 1330, the distance (D') between FIT' and FIT is calculated. At 1332, if D' is greater than a threshold (Epsilon), operations proceed to step 1334. Otherwise, operations return to step 1320. The default for Epsilon is 0.01. It should be understood that Epsilon can be more or less than 0.01. At 1334, if iteration is less than the maximum iteration number, operations proceed to step 1336. Otherwise, operations return to step 1320. At 1336, FIT' is assigned to FIT (i.e., FIT=FIT'). At 1338, the weight (W) for rotation is calculated and operations return to step 1326. At 1342, translation (T) is initialized with value 0 and distance (D) between FIT and FIX is calculated. At 1344, if D is greater than the adaptive threshold (β), operations proceed to step 1346. Otherwise, operations proceed to END (i.e., step 1312 is complete). At 1346, the weight for translation (a) is calculated. At 1348, translation (T) is calculated and applied to FIT (i.e., FIT'=T+FIT). At 1350, the distance (D') between FIT' and FIT is calculated. At 1352, if D' is greater than a threshold (Epsilon), operations proceed to step 1354. Otherwise, operations proceed to END (i.e., step 1312 is complete). At 1354, if iteration is less than the maximum iteration number, operations proceed to step 1356. Otherwise, operations proceed to END (i.e., step 1312 is complete). At 1356, FIT' is assigned to FIT (i.e., FIT=FIT'). At 1358, the weight (W) for rotation is calculated and operations proceed to END (i.e., step 1312 is complete).

Sub-operations for step 1314 are provided below. At 1362, FIT and FIT0 are averaged and stored (e.g., in memory) as MID. At 1364, a principal component decomposition of MID is performed. At 1366, vector (v) associated with the last component is stored as the plane of symmetry (e.g., midsagittal plane) normal. At 1368, the plane of symmetry normal is translated to pass through the center of MID and operations proceed to END (i.e., step 1314 is complete).

Symmetric Analysis

Figure 14:
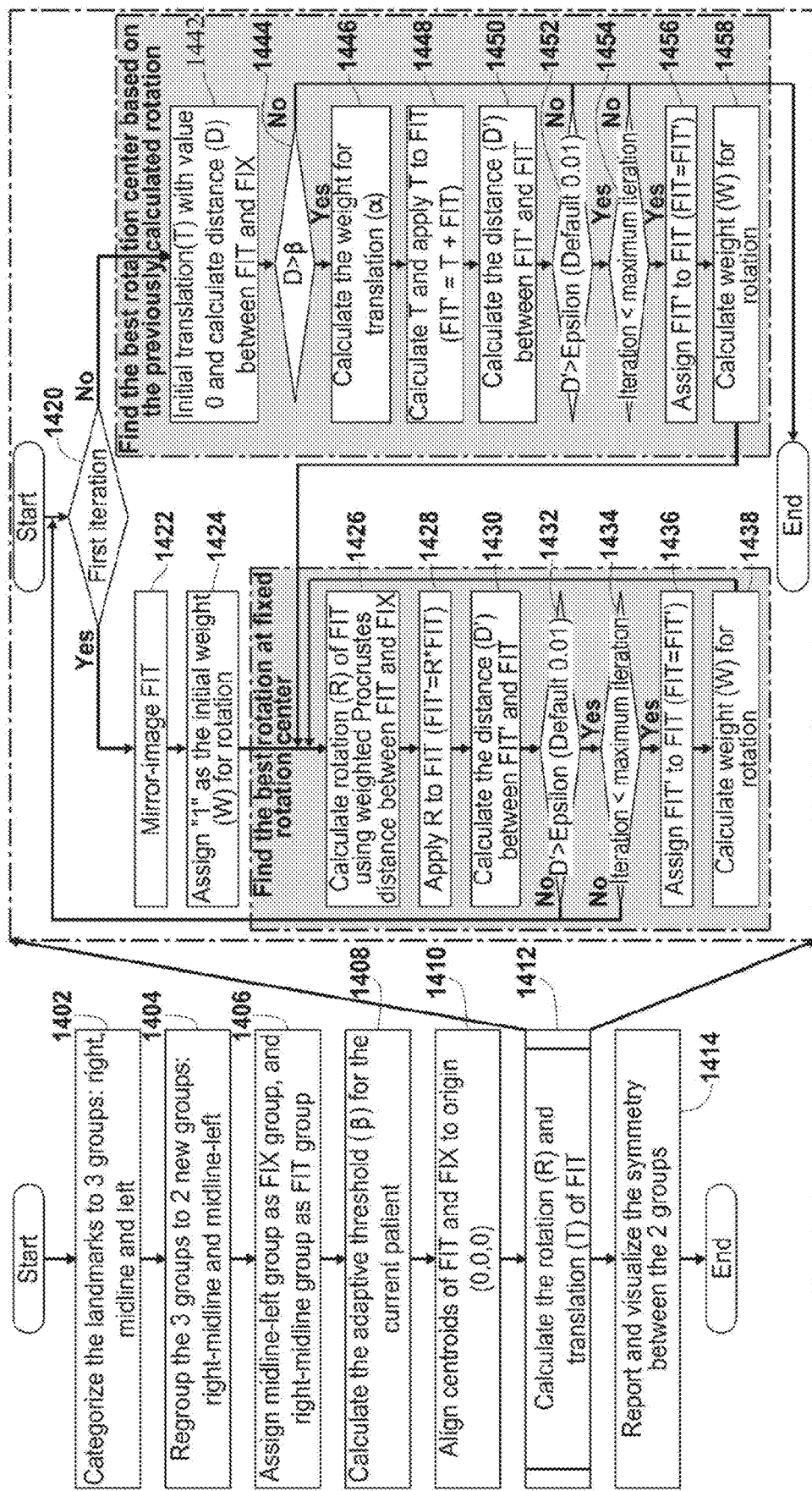
FIG. 14 is a flowchart illustrating example operations for calculating intrinsic symmetry according to an implementation described herein.

Techniques for performing a symmetric analysis are described below. As described above, the orthognathic surgical planning system and/or AnatomicAligner (as part of Module 3) can perform a symmetric analysis as part of the 3D cephalometric analysis. Two elements that relate to symmetry are: object symmetry and symmetrical alignment. Object symmetry refers to the intrinsic-mirror-symmetry that each facial unit should have. Symmetric alignment refers to the alignment of each facial unit with the midsagittal plane of the face (or composite 3D model thereof). An iterative weighted Procrustes superimposition of half forms algorithm for calculating intrinsic symmetry is described below with reference to FIG. 14. With reference to FIG. 14, example operations for calculating intrinsic symmetry of a three-dimensional (3D) model (e.g., the composite 3D model described above) are shown. This disclosure contemplates that the example operations shown in FIG. 14 can be performed, for example, using a computing device such as the computing device 1100 shown in FIG. 11.

At 1402, a plurality of landmarks are categorized into three groups: right, midline, and left. At 1404, the three groups of landmarks are regrouped into two groups: right-midline and midline-left. At 1406, the midline-left group is assigned as "FIX", and the right-midline group is assigned as "FIT". At 1408, an adaptive threshold ($\beta$) for the subject (i.e., patient specific) is calculated. The adaptive threshold ($\beta$) is calculated. At 1410, centroids of FIT and FIX are aligned to the origin (0, 0, 0). At 1412, rotation (R) and translation (T) of FIT are calculated. At 1414, the symmetry between the two groups (i.e., FIT and FIX) is calculated and operations proceed to END (i.e., step 1414 is complete). Optionally, as described above, this symmetry measure can be provided as part of the 3D cephalometric report.

Sub-operations for step 1412 are provided below. At 1420, for the first iteration, operations proceed to step 1422. These operations find the best rotation (R) at fixed rotation center. For subsequent iterations, operations instead proceed to step 1442. These operations find the best rotation center based on the previously determined rotation (R). For the first iteration, at 1422, a mirror image copy of FIT is created. The right-midline group (i.e., FIT) is mirror-imaged to the left in the example shown in FIG. 14. This disclosure contemplates that the midline-left group (i.e., FIX) can optionally be mirror imaged to the right in other implementations and operations adjusted accordingly. At 1424, the initial weight (W) for rotation (R) is assigned as "1". At 1426, rotation (R) of FIT is calculated using a weighted Procrustes distance between FIT and FIX. At 1428, rotation (R) is applied to FIT to obtain FIT' (i.e., FIT'=R*FIT). At 1430, the distance (D') between FIT' and FIT is calculated. At 1432, if D' is greater than a threshold (Epsilon), operations proceed to step 1434. Otherwise, operations return to step 1420. At 1434, if iteration is less than the maximum iteration number, operations proceed to step 1436. Otherwise, operations return to step 1420. At 1436, FIT' is assigned to FIT (i.e., FIT=FIT'). At 1438, the weight (W) for rotation is calculated and operations return to step 1426. At 1442, translation (T) is initialized with value 0 and distance (D) between FIT and FIX is calculated. At 1444, if D is greater than the adaptive threshold ($\beta$), operations proceed to step 1446. Otherwise, operations proceed to END (i.e., step 1412 is complete). At 1446, the weight for translation (a) is calculated. At 1448, translation (T) is calculated and applied to FIT (i.e., FIT'=T+FIT). At 1450, the distance (D') between FIT' and FIT is calculated. At 1452, if D' is greater than a threshold (Epsilon), operations proceed to step 1454. Otherwise, operations proceed to END (i.e., step 1412 is complete). At 1454, if iteration is less than the maximum iteration number, operations proceed to step 1456. Otherwise, operations proceed to END (i.e., step 1412 is complete). At 1456, FIT' is assigned to FIT (i.e., FIT=FIT'). At 1458, the weight (W) for rotation is calculated and operations proceed to END (i.e., step 1412 is complete).

Splint Design

Techniques for designing a surgical splint or template are described below. As described above, the orthognathic surgical planning system and/or AnatomicAligner (as part of Module 6) can be used to design a surgical splint, which is the horseshoe-shaped teeth-anchored wafer that is placed between the subject's upper and lower teeth during surgery.

Figure 15:
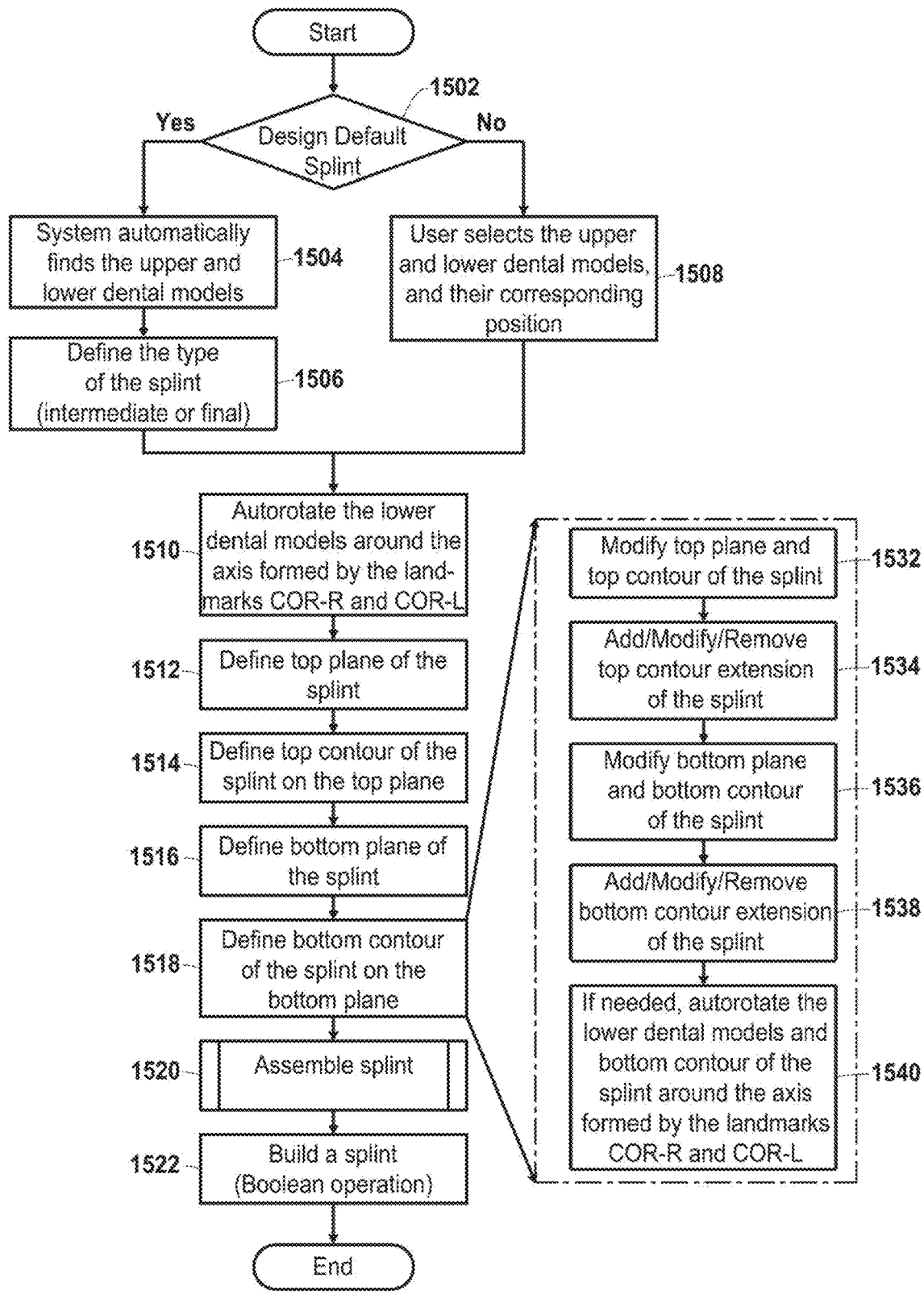
FIG. 15 is a flowchart illustrating example operations for designing a surgical splint according to an implementation described herein.

With reference to FIG. 15, example operations for designing a surgical splint are shown. This disclosure contemplates that the example operations shown in FIG. 15 can be performed, for example, using a computing device such as the computing device 1100 shown in FIG. 11. At 1502, if upper and lower dental models (e.g., high resolution upper and lower digital dental models as described herein) are to be automatically selected, operations proceed to step 1504. At 1504, the upper and lower dental models are identified automatically by the system. At 1506, the type of surgical splint is defined, e.g., intermediate splint for maxillary surgery first, intermediate splint for mandibular surgery first, or final splint. Otherwise, operations proceed to operation 1508, where a user manually selects the upper and lower dental arches. Optionally, for an intermediate splint, at 1510, the lower dental model is autorotated around the center of rotation of the right mandibular condyle (COR-R) and around the center of rotation of the left mandibular condyle (COR-L). At 1512, a top plane of the splint is defined. This can be performed by digitizing a plurality of landmarks on the occlusal surface of the upper dental arch to form a top plane for the splint. At 1514, a top contour for the top plane of the splint is defined. This can be performed by tracing the upper dental arch onto top plane. An example top contour 802 is shown in FIGS. 8A-8B. At 1516, a bottom plane of the splint is defined. This can be performed by digitizing a plurality of landmarks on the occlusal surface of the lower dental arch to form a bottom plane for the splint. At 1518, a bottom contour for the bottom plane of the splint is defined. This can be performed by copying the top contour to the bottom plane, forming the bottom contour, for the bottom face of the splint. An example bottom contour 804 is shown in FIG. 8B. At 1520, the raw splint model is assembled. An example surface model of the raw splint as shown in FIG. 8B. At 1522, the splint model is generated by Boolean operation, e.g., by subtracting the upper and lower teeth from the splint model. The surgical splint can then be printed, e.g., using a 3D printer.

Sub-operations for step 1518 are described below. At 1532, the top plane and top contour of the splint can be modified. Optionally, at 1534, top contour extensions (e.g., contour extension 802a shown in FIG. 8B) can be added, modified, or removed. At 1536, the bottom plane and bottom contour of the splint can be modified. Optionally, at 1538, bottom contour extensions (e.g., contour extension 804a shown in FIG. 8B) can be added, modified, or removed. Optionally, at 1540, the lower dental model and bottom contour of the splint are autorotated around the center of rotation of the right mandibular condyle (COR-R) and around the center of rotation of the left mandibular condyle (COR-L), if needed.

Overcorrection

Techniques for overcorrection are described below. The orthognathic surgical planning system and/or AnatomicAligner can be used to perform overcorrection of distal and/or proximal segments of a 3D model of the subject's mandible.

Figure 16:
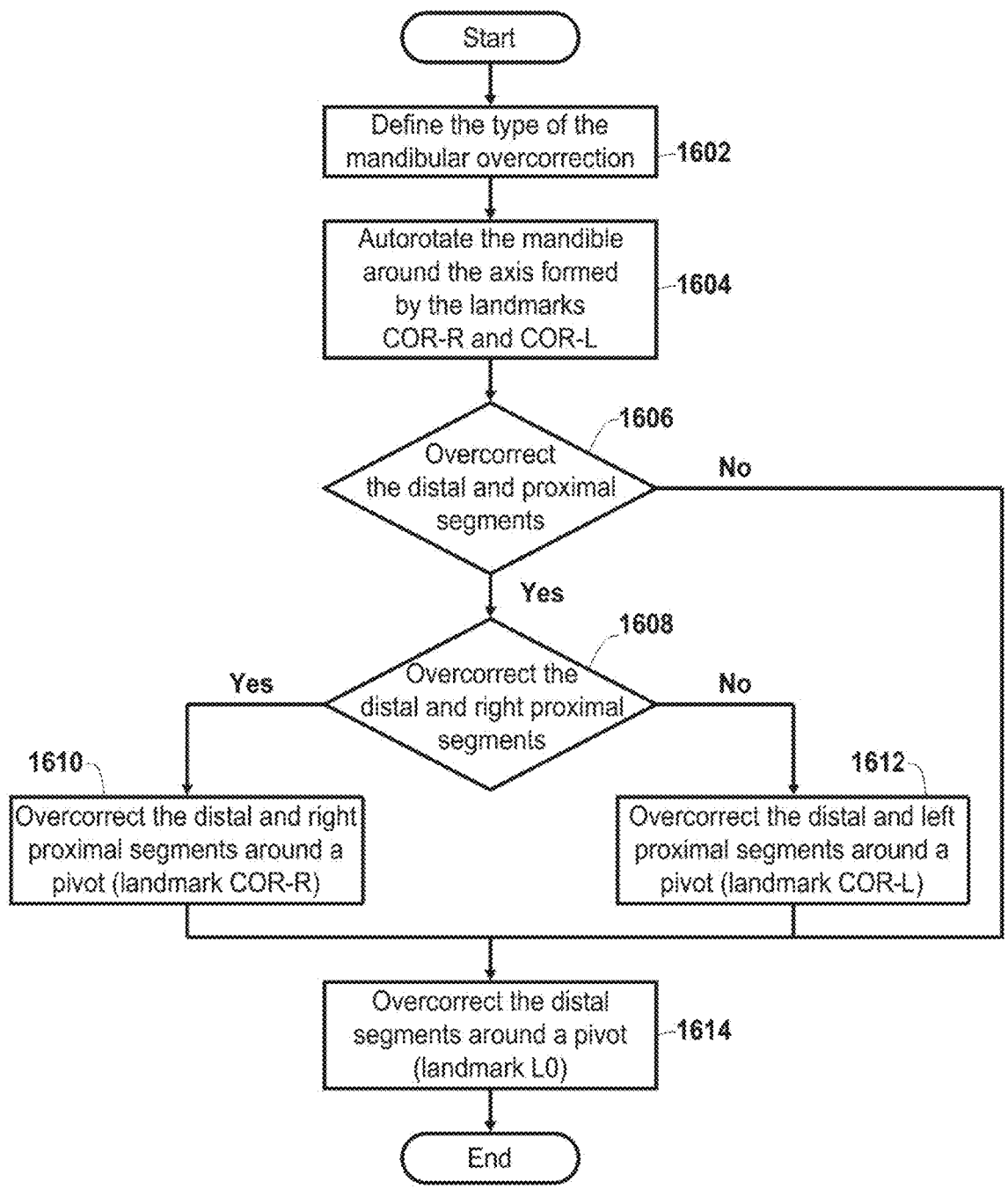
FIG. 16 is a flowchart illustrating example operations for performing overcorrection according to an implementation described herein.

With reference to FIG. 16, example operations for overcorrection are shown. This disclosure contemplates that the example operations shown in FIG. 16 can be performed, for example, using a computing device such as the computing device 1100 shown in FIG. 11. At 1602, a type of mandibular overcorrection is defined. At 1604, the mandible (e.g., the 3D model of the subject's mandible) is autorotated around the center of rotation of the right mandibular condyle (COR-R) and around the center of rotation of the left mandibular condyle (COR-L). At 1606, if both distal and proximal segments are to be overcorrected, then operations proceed to step 1608. Otherwise, operations proceed to step 1614, where the distal segments are overcorrected around a pivot. At step 1608, if the distal and right proximal segments are to be overcorrected, then operations proceed to step 1610, where the distal and right proximal segments are overcorrected around a pivot (e.g., COR-R). At step 1608, if the distal and left proximal segments are to be overcorrected, then operations proceed to step 1612, where the distal and left proximal segments are overcorrected around a pivot (e.g., COR-L). At 1614, the distal segments are overcorrected around a pivot.

Object Reference Frame for Dental Arch

Techniques for establishing an object reference frame for dental arch are described below. The orthognathic surgical planning system and/or AnatomicAligner (e.g., as part of module 3) can be used to establish an object reference frame for dental arch.

For example, a principal component analysis-based adaptive minimum Euclidean distances (PAMED) approach to establish an optimal object reference frame for symmetrical alignment of the dental arch during computer-aided surgical simulation (CASS) has been developed. As described above, during cephalometric analysis, the object reference frame can be established using the PAMED algorithm. As compared to triangular and standard PCA methods, the PAMED approach is the most reliable and consistent approach for establishing the object reference frame for the dental arch in orthognathic surgical planning. For example, the triangular method is not reliable when there is dental arch asymmetry of any etiology, for example, unilateral edentulism, or individual tooth misalignment. Any of the above conditions can skew the triangular method and cause errors in defining the object reference frame.

An important step in orthognathic surgical planning is to restore the symmetrical alignment of a dental arch with reference to the whole face [33-36]. Analyzing dental arch symmetrical alignment requires an object reference frame, previously called a local coordinate system or a local reference frame. Like the global reference frame for the whole face, the object reference frame for a dental arch is composed of three orthogonal planes. The axial plane divides the dental arch into upper and lower halves; the coronal plane divides the arch into front and back halves; and the midsagittal plane evenly divides the arch into right and left halves evenly. By comparing the object reference frame for the dental arch to the global reference frame for the whole face, the symmetrical alignment of the dental arch can be calculated as a transverse difference in the central incisal midpoint (dental midline), and orientational differences in yaw and roll (cant).

The PAMED approach described herein was programmed using MATLAB 2014a from The MathWorks, Inc. of Natick, MA, and the calculation was completed in real time. It should be understood that the PAMED algorithm can be implemented using hardware and/or software other than those described in the example below. Additionally, the PAMED algorithm uses the landmarks provided in Table 2 below. The PAMED algorithm uses more dental landmarks as compared to the triangular method, which improves the accuracy of establishing an object reference frame for the dental arch.

TABLE 2

Definition of the landmarks used in the computation.

| Landmark | Definition |
| --- | --- |
| U0 | The midpoint between the two central incisal edges |
| U2 | The midpoint on the lateral incisal edge |
| U3 | The tip of the canine |
| U4 | The buccal cusp of the first premolar |
| U5 | The buccal cusp of the second premolar |
| U6 | The mesiobuccal cusp of the first molar |
| U7 | The mesiobuccal cusp of the second molar |

An important step in orthognathic surgical planning is to establish a correct object reference frame of the dental arch during symmetrical alignment. Owing to the nature of the dental arch, the occlusal plane is often used as the axial plane. Once the midsagittal plane is correctly defined, it is not difficult to define the coronal plane. It is always mutually perpendicular to both the axial and midsagittal planes and passes through U0.

Defining the midsagittal plane is the key to establishing the object reference frame for the dental arch. The PAMED approach described herein is the most consistent method of creating the midsagittal plane for the dental arch, even in the presence of a unilateral missing tooth or individual tooth misalignment. The triangular method performs reasonably well in generating the midsagittal plane because the two posterior landmarks are digitized "dynamically". Instead of statically using the two mesiobuccal cusps of the first molars, the evaluators may have to change landmarks in order to form a hypothetical isosceles triangle representing an arch, for example using either the mesiobuccal cusps of the second molars or the second premolars [34]. As expected, when using the triangular method, the midsagittal plane is affected by the presence of a unilateral missing tooth (1/30) and individual tooth misalignment (1/30). Finally, the standard PCA method is the least reliable method.

The standard PCA method is less reliable than the triangular method. This is because PCA is a statistical procedure that uses an orthogonal transformation to convert a set of observations of possibly correlated variables into a set of values of linearly uncorrelated variables, the principal components (vectors). Thus, the origin of the three orthogonal principal components is located in the middle of the dental arch. Although two principal components (Y- and Z-axes) are assigned to be the midsagittal plane, it may not necessarily pass through U0. When used in CASS surgical planning, the origin must be translated to U0, causing the midsagittal plane to be shifted towards one side. In addition, the standard PCA method is sensitive to the landmarks used for the computation because it only uses up to 13 dental landmarks. Any outlier may significantly skew the result. Although the PAMED approach is also based on the PCA method to determine the occlusal plane, the Y-axis for the midsagittal plane is iteratively recomputed by minimizing the Euclidian distances between the right and left dental curves. The PAMED method also has solved the outlier problem by resampling the 13 dental landmarks to 1,399 points.

There are two definitions to define an occlusal plane. Traditionally, an occlusal plane passes through the central incisal edges and the mesiobuccal cusps of the first molars. This fits the definition of the triangular method. However, it is sensitive to the landmarks used to construct the triangle. The object reference frame can be affected by outliers in the triangular method if an overerupted or impacted tooth is used. The occlusal plane is better defined when it evenly passes through all edges and cusps. This fits the definition of PAMED and the standard PCA methods: the X'O'Y' plane is constructed by the first and second principal components.

Figure 17:
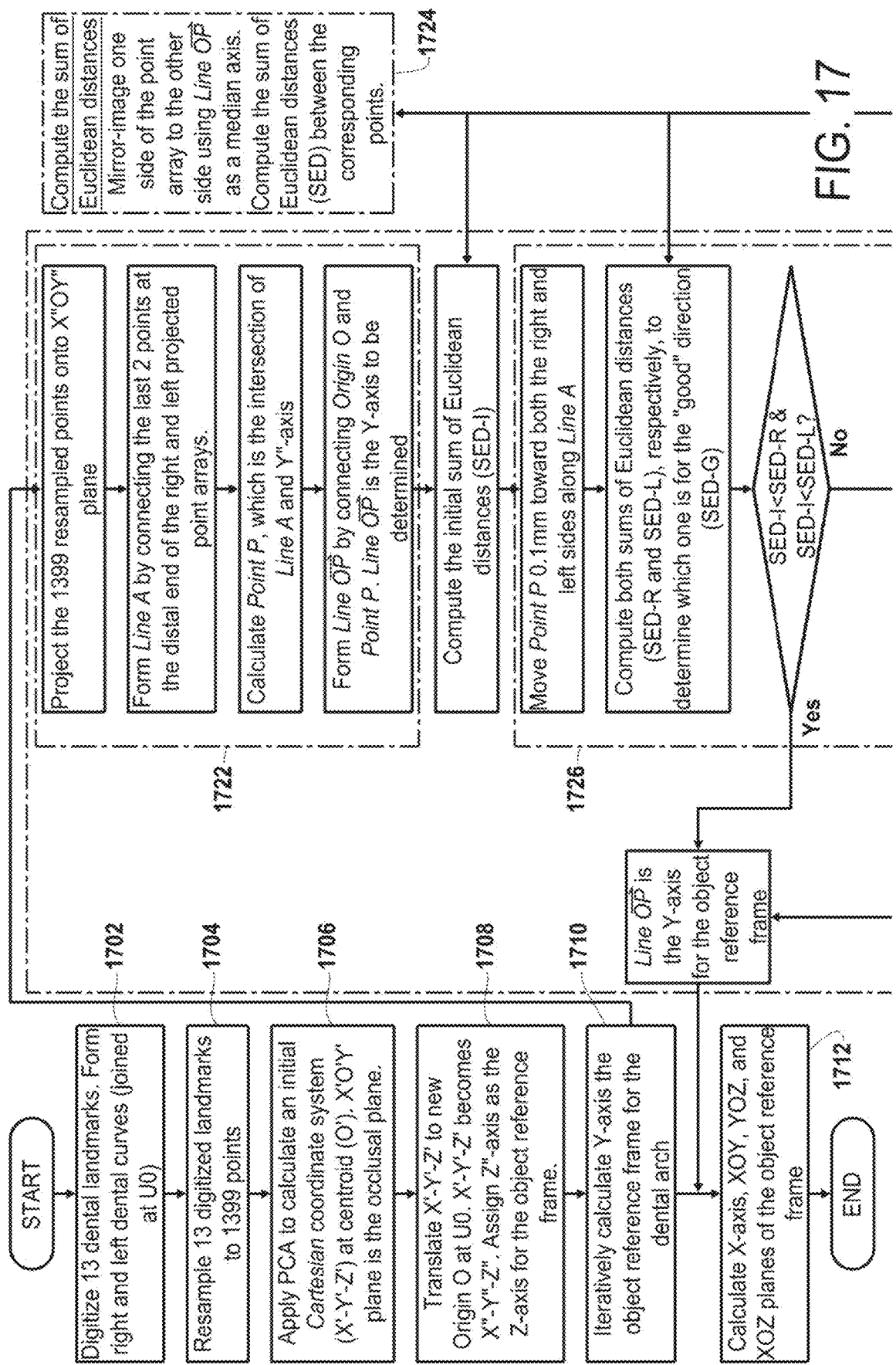
FIG. 17 is a flowchart illustrating example operations for establishing an object reference frame for dental arch using a principal component analysis-based adaptive minimum Euclidean distances (PAMED) algorithm.
Figure 17:
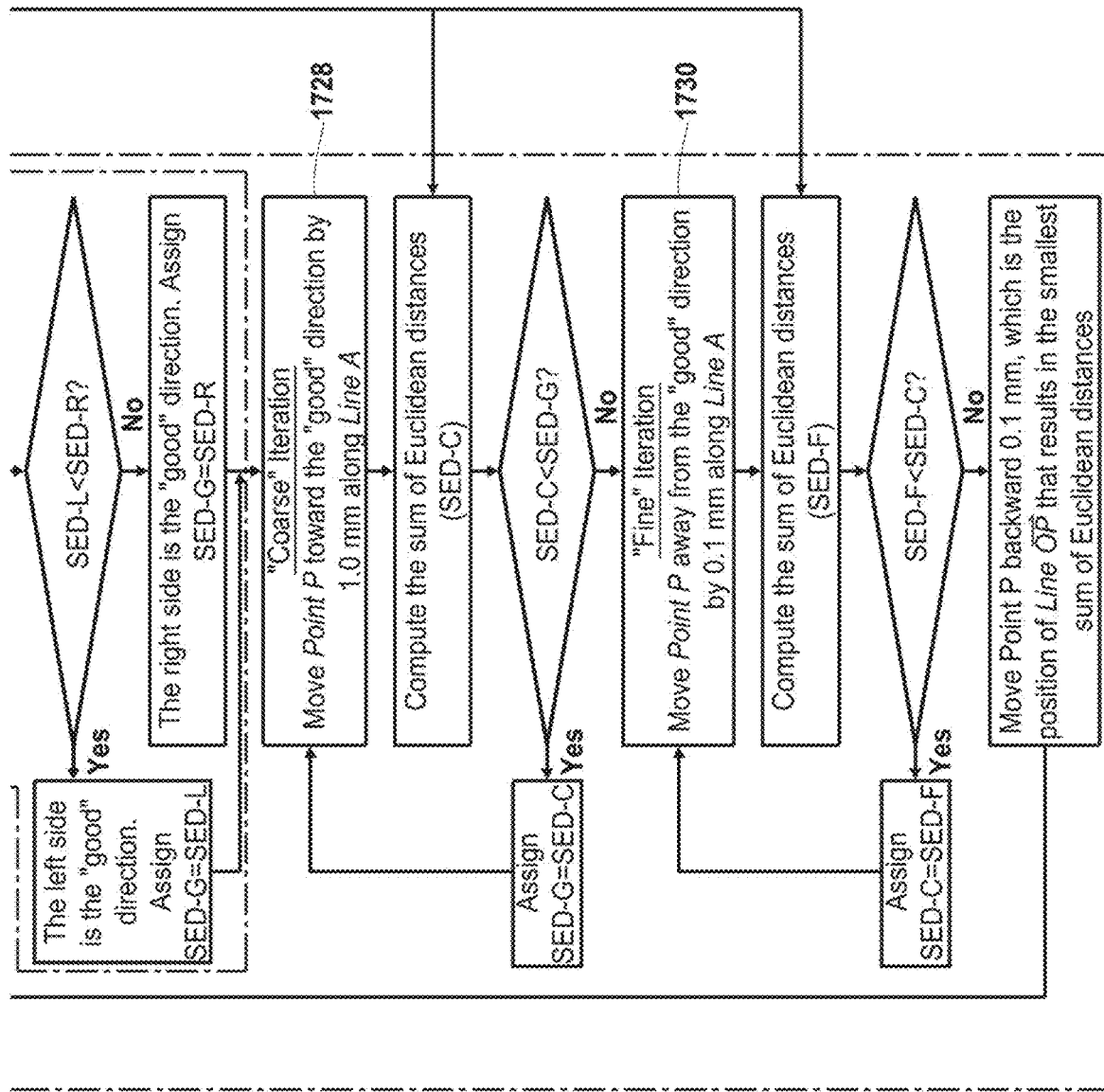

With reference to FIG. 17, example operations for establishing an object reference frame for dental arch using the PAMED algorithm are shown. The key to the PAMED approach is to find the optimal minimum for the midsagittal plane, which evenly divides the dental arch into the right and left halves.

Figure 18A:
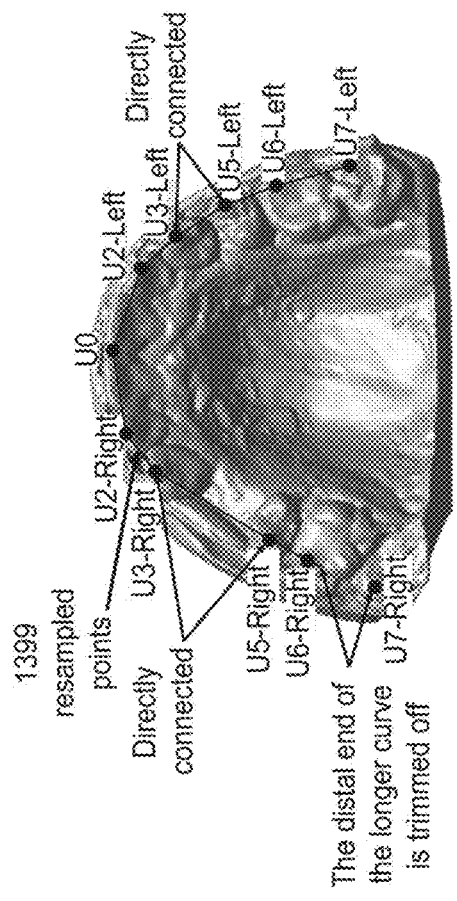
FIGS. 18A-18H illustrate the PAMED approach.
Figure 18B:
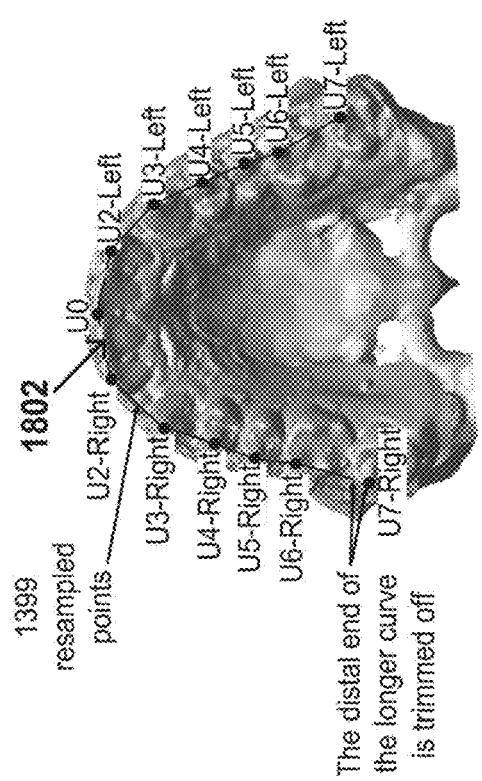

At 1702, a plurality of landmarks are digitized and right and left dental curves are formed. In FIG. 17, thirteen dental landmarks are digitized on a maxillary dental arch, six landmarks on each side with one in the middle. The landmarks are listed in Table 2 above and also shown in FIG. 18A. The midpoint U0 represents the central dental midpoint. The 13 digitized dental landmarks are then connected to form a right and a left dental curve, seven points (U0, U2-U7) on each side. The first point of both right and left curves is U0. Since U0 is derived from the right and left central incisors (U1), both the right and left U1 are not used in the calculation. In cases of a missing tooth, its landmark is not digitized and the two adjacent landmarks are directly connected as shown in FIG. 18B.

At 1704, the digitized landmarks are resampled. The Euclidian distances of the right and left dental curves are computed respectively. The distal (molar) end of the longer curve is then trimmed off, making the right and left curves equal-distance as shown in FIG. 18A. The right and left curves are then evenly resampled to 700 points on each side, which yields approximately 0.1 mm of resampling resolution. The first points on each side of the point arrays are joined at U0, resulting in a total of 1,399 resampled points for the entire dental arch.

Figure 18C:
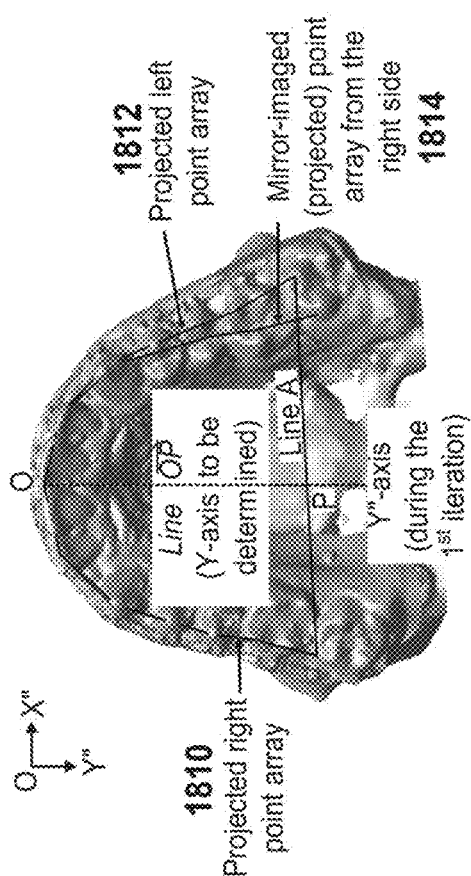

At 1706, PCA is applied to calculate an initial Cartesian coordinate system. A standard PCA is applied on the 1,399 resampled points, computing the first, second, and third principal components. They are mutually perpendicular to each other. The initial Cartesian coordination system (X'-Y'-Z') is determined as follows. The origin of the three principal components, located in the middle of the dental arch, is the origin O' of the initial Cartesian coordinate system as shown in FIG. 18C. The third principal component, the smallest variance, is defined as the Z'-axis. The first and second principal components are defined as the X'- and Y'-axes. The Y'-axis is the principal component that divides the 1,399 points in to the right and left groups, and the X'-axis is the last principal component. Finally, the X'O'Y' plane represents the occlusal plane, which evenly passes through all the edges and cusps.

At 1708, the origin is defined and Z-axis of the object reference frame is calculated. The origin O of the object reference frame for the dental arch is defined at U0. Therefore, the initial Cartesian coordinate system is translated into the new origin O at U0. Subsequently, the X'-, Y'- and Z'-axes become X"-, Y"-, and Z"-axes, and X'O'Y' plane becomes X"OY" plane as shown in FIG. 18C. Finally, the Z"-axis is assigned as the Z-axis of the object reference frame for the dental arch.

At 1710, the Y-axis for the object reference frame is iteratively calculated.

Figure 18D:
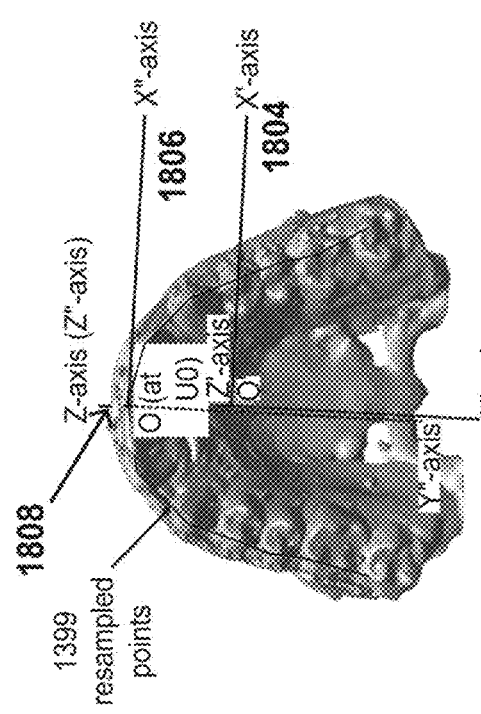

At 1722 (Initialization), the 1399 resampled points are projected onto X"OY" plane along the Z-axis. The last two points at the distal end of the right and left projected point arrays are connected to form Line A. Point P is the intersection point of Line A and Y"-axis as shown in FIG. 18D. The Origin O and Point P are then connected to form Line $\vec{OP}$. It will be the Y-axis for the object reference frame of the dental arch. During the first iteration, Line $\vec{OP}$ is the Y"-axis as shown in FIG. 18D.

At 1724 (Computing the sum of Euclidean distances), on the X"OY" plane, the right side of the projected point array is the mirror image of the left around Line $\vec{OP}$. The initial sum of the Euclidean distances between the corresponding points are computed as shown in FIG. 18D.

Figure 18E:
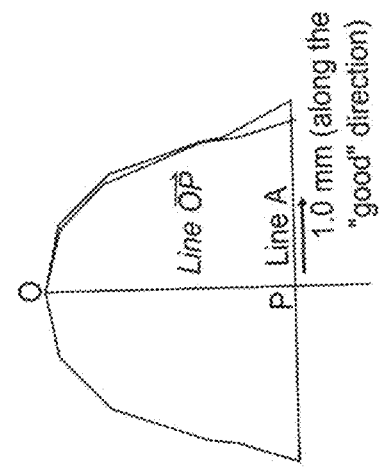

At 1726 (Initialization), Point P is moved 0.1 mm both right and left along line A. The sums of the Euclidean distances for both sides are calculated by repeating step 1724. They are compared with the initial sum of the Euclidean distances calculated in step 1724. The direction that results in a smaller sum of Euclidean distances is a "good" direction for step 1726 as shown in FIG. 18E. If the initial sum of the Euclidean distances calculated in step 1724 is the smallest among the three, Line $\vec{OP}$ becomes the Y-axis and the iteration stops and operations proceed to step 1712.

Figure 18F:
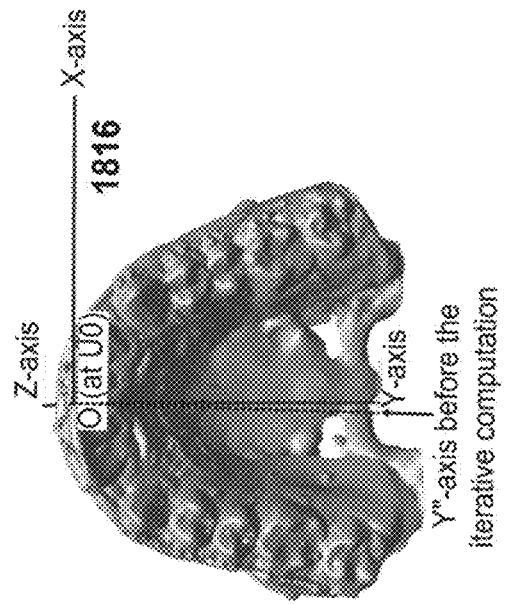

At 1728 ("Coarse" Iteration), Point P is moved continuously in 1.0-mm steps toward the "good" direction. Step 1724 is repeated until the sum of the Euclidean distances becomes larger as shown in FIG. 18F.

Figure 18G:
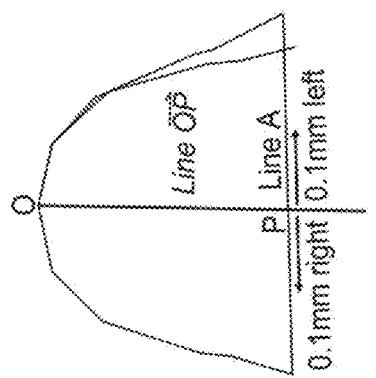

At 1730 ("Fine" Iteration), Point P is moved continuously in 0.1-mm steps opposite to the "good" direction. Step 1724 is repeated in order to calculate an optimal solution for Line $\vec{OP}$ until the sum of Euclidean distances becomes larger. Line $\vec{OP}$ that results in the smallest sum of distances, the optimal solution, is defined as Y-axis of the object reference frame as shown in FIG. 18G.

Figure 18H:
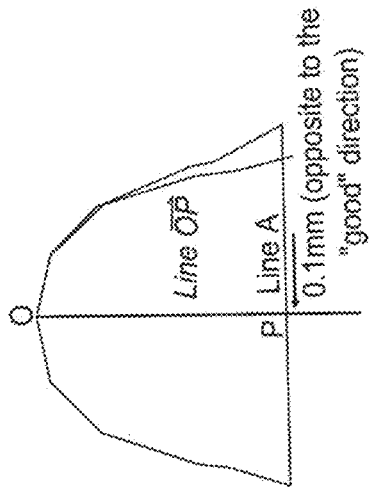

At 1712, the X-axis, and XOY, YOZ and XOZ planes of the object reference frame are calculated. The X-axis of the reference frame is perpendicular to both Y- and Z-axes as shown in FIG. 18H. The XOY (axial), YOZ (midsagittal), and XOZ (coronal) planes are finally computed based on the X-, Y- and Z-axes.

FIG. 18A illustrates thirteen dental landmarks digitized on the dental model. They form a right and a left curves 1802 joined at U0. The Euclidian distances are calculated for each curve. If the right and left Euclidian distances are not equal, the distal (molar) end of the longer curve is then trimmed off, making the right and left curves equal-distance. The entire dental curve is evenly resampled to 1,399 points (black dots on the curves). FIG. 18B illustrates the two first premolars are missing in a dental arch of an obstructive sleep apnea patient. The landmarks for the missing teeth are not digitized and the 2 adjacent landmarks are directly connected. FIG. 18C illustrates a standard PCA applied to an initial Cartesian coordinate system (X'-Y'-Z'). The origin O' is located in the middle of the dental arch. The X'O'Y' plane 1804 is the occlusal plane. The initial Cartesian coordinate system is then translated to the new origin O at U0. Subsequently, X'-, Y'-, and Z'-axes become X"-, Y"- and Z"-axes 1808, and X'O'Y' plane becomes X"OY" plane 1806. Finally, the Z"-axis is assigned as the Z-axis of the object reference frame for the dental arch. FIG. 18D illustrates the Y-axis of the reference frame for the dental arch is computed iteratively. The resampled points are projected onto X"OY" plane along Z-axis. The right point array is 1810 and the left point array is 1812. Line A connects the last two points at the distal end of the right and left projected point arrays. Point P is the intersection point of Line A and Y"-axis. The Origin O and Point P are connected to form Line $\vec{OP}$, which is the Y-axis to be determined. During the first iteration, Line $\vec{OP}$ is Y"-axis. The right side of the point array is mirror-imaged to the other side around the Line $\vec{OP}$ on X"OY" plane as shown by 1814. The sum of Euclidean distances between the corresponding points of the left point array 1812 and the mirror-imaged right point array 1814 are calculated. FIG. 18E illustrates how to find a "good" direction. Point P is moved 0.1 mm toward the right and left along line A. The sum of the Euclidean distances is calculated as in step 1724 of FIG. 17. The direction that can result in a smaller sum of Euclidean distances is a "good" direction for the next step. In this example, the left is the "good" direction. FIG. 18F illustrates the "Corse" Iteration: Point P is moved continuously toward the "good" direction in 1.0 mm steps. Step 1724 of FIG. 17 is repeated until the sum of Euclidean distances becomes larger. FIG. 18G illustrates the "Fine" Iteration: point P is then moved continuously opposite to the "good" direction in a step of 0.1 mm to find the optimal solution for Line $\vec{OP}$. Step 1724 of FIG. 17 is repeated until the sum of Euclidean distances becomes larger. Line $\vec{OP}$ that results in the smallest sum of distances is defined as Y-axis of the object reference frame for the dental arch. FIG. 18H illustrates the object reference frame of dental arch 1816 established using the PAMED method. An axis 1818 indicates the original Y"-axis prior to the iterative calculation.

REFERENCES

1. Bell W H (1980) Surgical correction of dentofacial deformities. WB Saunders, Philadelphia
2. Bell W H (1992) Modern practice in orthognathic and reconstructive surgery. WB Saunders, Philadelphia
3. Xia J J, Gateno J, Teichgraeber J F (2009) New clinical protocol to evaluate craniomaxillofacial deformity and plan surgical correction. J Oral Maxillofac Surg 67 (10): 2093-2106
4. Xia J J, Gateno J, Teichgraeber J F, Yuan P, Chen K C, Li J, Zhang X, Tang Z, Alfi D M (2015) Algorithm for planning a double-jaw orthognathic surgery using a computer-aided surgical simulation (CASS) protocol. Part 1: planning sequence. Int J. Oral Maxillofac Surg 44 (12): 1431-1440. doi:10.1016/j.ijom.2015.06.006
5. Bobek S, Farrell B, Choi C, Farrell B, Weimer K, Tucker M (2015) Virtual surgical planning for orthognathic surgery using digital data transfer and an intraoral fiducial marker: the charlotte method. J Oral Maxillofac Surg 73 (6):1143-1158. doi:10.1016/j.joms.2014.12.008
6. Hsu S S, Gateno J, Bell R B, Hirsch D L, Markiewicz M R, Teichgraeber J F, Zhou X, Xia J J (2013) Accuracy of a computer-aided surgical simulation protocol for orthognathic surgery: a prospective multicenter study. J Oral Maxillofac Surg 71 (1):128-142. doi:10.1016/j.joms.2012.03.027
7. Yuan P, Ho D C-Y, Chang C-M, Li J, Mai H, Kim D, Shen S, Zhang X, Zhou X, Xiong Z, Gateno J, Xia J J (2016) A Novel Computer-Aided Surgical Simulation (CASS) System to Streamline Orthognathic Surgical Planning. In: Zheng G, Liao H, Jannin P, Cattin P, Lee S-L (eds) Medical Imaging and Augmented Reality: 7th International Conference, MIAR 2016, Bern, Switzerland, Aug. 24-26, 2016, Proceedings. Springer International Publishing, Cham, pp 3-14. doi:10.1007/978-3-319-43775-0_1
8. Gateno J, Xia J, Teichgraeber J F, Rosen A (2003) A new technique for the creation of a computerized composite skull model. J Oral Maxillofac Surg 61 (2):222-227
9. Xia J J, Gateno J, Teichgraeber J F, Yuan P, Li J, Chen K C, Jajoo A, Nicol M, Alfi D M (2015) Algorithm for planning a double-jaw orthognathic surgery using a computer-aided surgical simulation (CASS) protocol. Part 2: three-dimensional cephalometry. Int J Oral Maxillofac Surg 44 (12):1441-1450. doi:10.1016/j.ijom.2015.06.007
10. Gateno J, Jajoo A, Nicol M, Xia J J (2016) The primal sagittal plane of the head: a new concept. Int J Oral Maxillofac Surg 45 (3):399-405. doi:10.1016/j.ijom.2015.11.013
11. Schatz E C (2006) A new technique for recording natural head position in three dimensions (MS thesis). The University of Texas Health Science Center at Houston, Houston (Advisors: Xia J J, English J D, Garrett F A, et al)
12. Schatz E C, Xia J J, Gateno J, English J D, Teichgraeber J F, Garrett F A (2010) Development of a technique for recording and transferring natural head position in 3 dimensions. J Craniofac Surg 21 (5):1452-1455. doi: 10.1097/SCS.0b013e3181ebcd0a
13. Xia J J, McGrory J K, Gateno J, Teichgraeber J F, Dawson B C, Kennedy K A, Lasky R E, English J D, Kau C H, McGrory K R (2011) A new method to orient 3-dimensional computed tomography models to the natural head position: a clinical feasibility study. J Oral Maxillofac Surg 69 (3):584-591. doi:10.1016/j.joms.2010.10.034
14. Gateno J, Xia J J, Teichgraeber J F (2011) New 3-dimensional cephalometric analysis for orthognathic surgery. J Oral Maxillofac Surg 69 (3):606-622. doi:10.1016/j.joms.2010.09.010
15. Gateno J, Xia J J, Teichgraeber J F, Christensen A M, Lemoine J J, Liebschner M A, Gliddon M J, Briggs M E (2007) Clinical feasibility of computer-aided surgical simulation (CASS) in the treatment of complex craniomaxillofacial deformities. J Oral Maxillofac Surg 65 (4):728-734
16. Xia J, Ip H H, Samman N, Wang D, Kot C S, Yeung R W, Tideman H (2000) Computer-assisted three-dimensional surgical planning and simulation: 3D virtual osteotomy. Int J Oral Maxillofac Surg 29 (1):11-17
17. Xia J, Ip H H, Samman N, Wong H T, Gateno J, Wang D, Yeung R W, Kot C S, Tideman H (2001) Three-dimensional virtual-reality surgical planning and soft-tissue prediction for orthognathic surgery. IEEE Trans Int Technol Biomed 5 (2):97-107
18. Xia J J, Gateno J, Teichgraeber J F (2005) Three-dimensional computer-aided surgical simulation for maxillofacial surgery. Atlas Oral Maxillofac Surg Clin North Am 13 (1):25-39
19. Gateno J, Xia J, Teichgraeber J F, Rosen A, Hultgren B, Vadnais T (2003) The precision of computer-generated surgical splints. J Oral Maxillofac Surg 61 (7):814-817
20. Swennen G R, Barth E L, Eulzer C, Schutyser F (2007) The use of a new 3D splint and double CT scan procedure to obtain an accurate anatomic virtual augmented model of the skull. Int J Oral Maxillofac Surg 36 (2):146-152
21. Lorensen W E, Cline H E Marching cubes: A high resolution 3D surface construction algorithm. In: SIGGRAPH '87 Proceedings of the 14th Annual Conference on Computer Graphics and Interactive Techniques, New York, NY, 1987. ACM SIGGRAPH Computer Graphics,
22. Xia J, Samman N, Yeung R W, Shen S G, Wang D, Ip H H, Tideman H (2000) Three-dimensional virtual reality surgical planning and simulation workbench for orthognathic surgery. Int J Adult Orthodon Orthognath Surg 15 (4):265-282
23. Damstra J, Fourie Z, Ren Y (2010) Simple technique to achieve a natural position of the head for cone beam computed tomography. Br J Oral Maxillofac Surg 48 (3):236-238. doi:10.1016/j.bjoms.2009.10.001
24. Gateno J, Xia J J, Teichgraeber J F (2011) New Methods to Evaluate Craniofacial Deformity and to Plan Surgical Correction. Semin Orthod 17 (3):225-234. doi:10.1053/j.sodo.2011.02.006
25. Athanasiou A E (1995) Orthodontic cephalometry. Mosby-Wolfe, St. Louis
26. Gateno J, Xia J J, Teichgraeber J F (2011) Effect of facial asymmetry on 2-dimensional and 3-dimensional cephalometric measurements. J Oral Maxillofac Surg 69 (3): 655-662. doi:10.1016/j.joms.2010.10.046
27. Swennen G R, Schutyser F (2006) Three-dimensional cephalometry: spiral multi-slice vs cone-beam computed tomography. Am J Orthod Dentofacial Orthop 130 (3): 410-416
28. Swennen G R, Schutyser F, Barth E L, De Groeve P, De Mey A (2006) A new method of 3-D cephalometry Part I: the anatomic Cartesian 3-D reference system. J Craniofac Surg 17 (2):314-325
29. Zelditch M L, Swiderski D L, Sheets H D (2012) Geometric morphometrics for biologists: a primer. Elsevier, London, UK
30. Gottschalk S, Lin M C, Manocha D (1996) OBBTree: a hierarchical structure for rapid interference detection. Paper presented at the Proc. of ACM Siggraph '96,
31. Chang Y B, Xia J J, Gateno J, Xiong Z, Zhou X, Wong S T (2010) An automatic and robust algorithm of reestablishment of digital dental occlusion. IEEE Trans Med Imaging 29 (9):1652-1663. doi:10.1109/TMI.2010.2049526
32. Chang Y B, Xia J J, Gateno J, Xiong Z, Teichgraeber J F, Lasky R E, Zhou X (2012) In vitro evaluation of new approach to digital dental model articulation. J Oral Maxillofac Surg 70 (4):952-962. doi:10.1016/j.joms.2011.02.109
33. Gateno, J., Xia, J. J., and Teichgraeber, J. F. New 3-dimensional cephalometric analysis for orthognathic surgery. *J Oral Maxillofac Surg.* 2011; 69: 606-622
34. Xia, J. J., Gateno, J., Teichgraeber, J. F., Yuan, P., Chen, K. C., Li, J., Zhang, X., Tang, Z., and Alfi, D. M. Algorithm for planning a double-jaw orthognathic surgery using a computer-aided surgical simulation (CASS) protocol. Part 1: planning sequence. *Int J Oral Maxillofac Surg.* 2015; 44: 1431-1440
35. Xia, J. J., Gateno, J., and Teichgraeber, J. F. New clinical protocol to evaluate craniomaxillofacial deformity and plan surgical correction. *J Oral Maxillofac Surg.* 2009; 67: 2093-2106
36. Xia, J. J., Gateno, J., Teichgraeber, J. F., Yuan, P., Li, J., Chen, K. C., Jajoo, A., Nicol, M., and Alfi, D. M. Algorithm for planning a double-jaw orthognathic surgery using a computer-aided surgical simulation (CASS) protocol. Part 2: three-dimensional cephalometry. *Int J Oral Maxillofac Surg.* 2015; 44: 1441-1450

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computer-implemented method for defining a primal reference frame for a three-dimensional (3D) model, comprising:
   identifying a plurality of landmarks on the 3D model, wherein the landmarks define a cloud of points;
   creating a mirror-image copy of the cloud of points;
   iteratively translating and/or rotating the mirror-image copy until fitted with the cloud of points;
   superimposing the mirror-image copy and the cloud of points to create a single group of points; and
   calculating a plane of symmetry that divides the single group of points, wherein iteratively translating and/or rotating the mirror-image copy until fitted with the cloud of points comprises calculating a weighted Procrustes distance between the mirror-image copy and the cloud of points.

2. The computer-implemented method of claim 1, wherein the 3D model is a composite 3D model of a subject's skull.

3. The computer-implemented method of claim 2, wherein the landmarks are features of the subject's skull.

4. The computer-implemented method of claim 2, wherein the plane of symmetry comprise a midsagittal plane, an axial plane, or a coronal plane.

* * * * *